(12) United States Patent
Ensign

(10) Patent No.: US 8,016,891 B2
(45) Date of Patent: Sep. 13, 2011

(54) TIBIAL AUGMENT CONNECTOR

(75) Inventor: Michael D. Ensign, Salt Lake City, UT (US)

(73) Assignee: Ortho Development Corporation, Draper, UT (US)

( * ) Notice: Subject to any disclaimer, the term of this patent is extended or adjusted under 35 U.S.C. 154(b) by 1377 days.

(21) Appl. No.: 11/241,251

(22) Filed: Sep. 30, 2005

(65) Prior Publication Data

US 2006/0100714 A1 May 11, 2006

Related U.S. Application Data

(63) Continuation of application No. PCT/US2004/001172, filed on Jan. 16, 2004.

(60) Provisional application No. 60/460,470, filed on Apr. 2, 2003, provisional application No. 60/464,870, filed on Apr. 22, 2003.

(51) Int. Cl.
*A61F 2/38* (2006.01)
(52) U.S. Cl. .................................................. 623/20.32
(58) Field of Classification Search .... 623/20.32–20.34; A61F 2/38
See application file for complete search history.

(56) References Cited

U.S. PATENT DOCUMENTS

| | | | |
|---|---|---|---|
| 3,774,244 A | 11/1973 | Walker | |
| 4,795,468 A * | 1/1989 | Hodorek et al. | 623/20.28 |
| 5,019,103 A | 5/1991 | Van Zile et al. | |
| 5,152,797 A * | 10/1992 | Luckman et al. | 623/20.16 |
| 5,171,276 A | 12/1992 | Caspari et al. | |
| 5,207,711 A | 5/1993 | Caspari et al. | |
| 5,236,461 A | 8/1993 | Forte | |
| 5,336,266 A | 8/1994 | Caspari et al. | |
| 5,358,527 A | 10/1994 | Forte | |
| 5,370,693 A | 12/1994 | Kelman et al. | |
| 5,387,241 A * | 2/1995 | Hayes | 623/20.16 |
| 5,458,637 A | 10/1995 | Hayes | |
| 5,458,645 A | 10/1995 | Bertin | |
| 5,480,445 A * | 1/1996 | Burkinshaw | 623/20.32 |
| 5,531,793 A | 7/1996 | Kelman et al. | |
| 5,800,552 A | 9/1998 | Forte | |
| 5,871,543 A * | 2/1999 | Hofmann | 623/20.32 |
| 6,102,955 A * | 8/2000 | Mendes et al. | 623/20.32 |
| 6,139,581 A | 10/2000 | Engh et al. | |
| 6,165,223 A | 12/2000 | Metzger et al. | 623/20.27 |
| 6,387,131 B1 * | 5/2002 | Miehlke et al. | 623/20.15 |
| 6,413,279 B1 | 7/2002 | Metzger et al. | |
| 6,503,280 B2 | 1/2003 | Repicci | |
| 2002/0082703 A1 | 6/2002 | Repicci | |
| 2002/0173852 A1 * | 11/2002 | Felt et al. | 623/20.32 |
| 2003/0093156 A1 * | 5/2003 | Metzger et al. | 623/20.15 |
| 2004/0030397 A1 * | 2/2004 | Collazo | 623/20.32 |

\* cited by examiner

*Primary Examiner* — David Isabella
*Assistant Examiner* — Jason-Dennis Stewart
(74) *Attorney, Agent, or Firm* — Matthew D. Thayne; Stoel Rives LLP

(57) ABSTRACT

An orthopedic augment member and connection to an implant is disclosed. The connection may be formed between the implant, comprising a recess with a ledge formed therein, and the augment member by utilizing a fastener, and a connector, which may be configured and dimensioned to snap-fit into the recess formed in the implant forming an interference fit therebetween. The fastener may further comprise a body member with threads located thereon for matingly engaging a threaded wall defining a recess formed in the augment member, thereby securing the augment member to the recess of the implant.

79 Claims, 17 Drawing Sheets

(Detail B)

(Detail B)

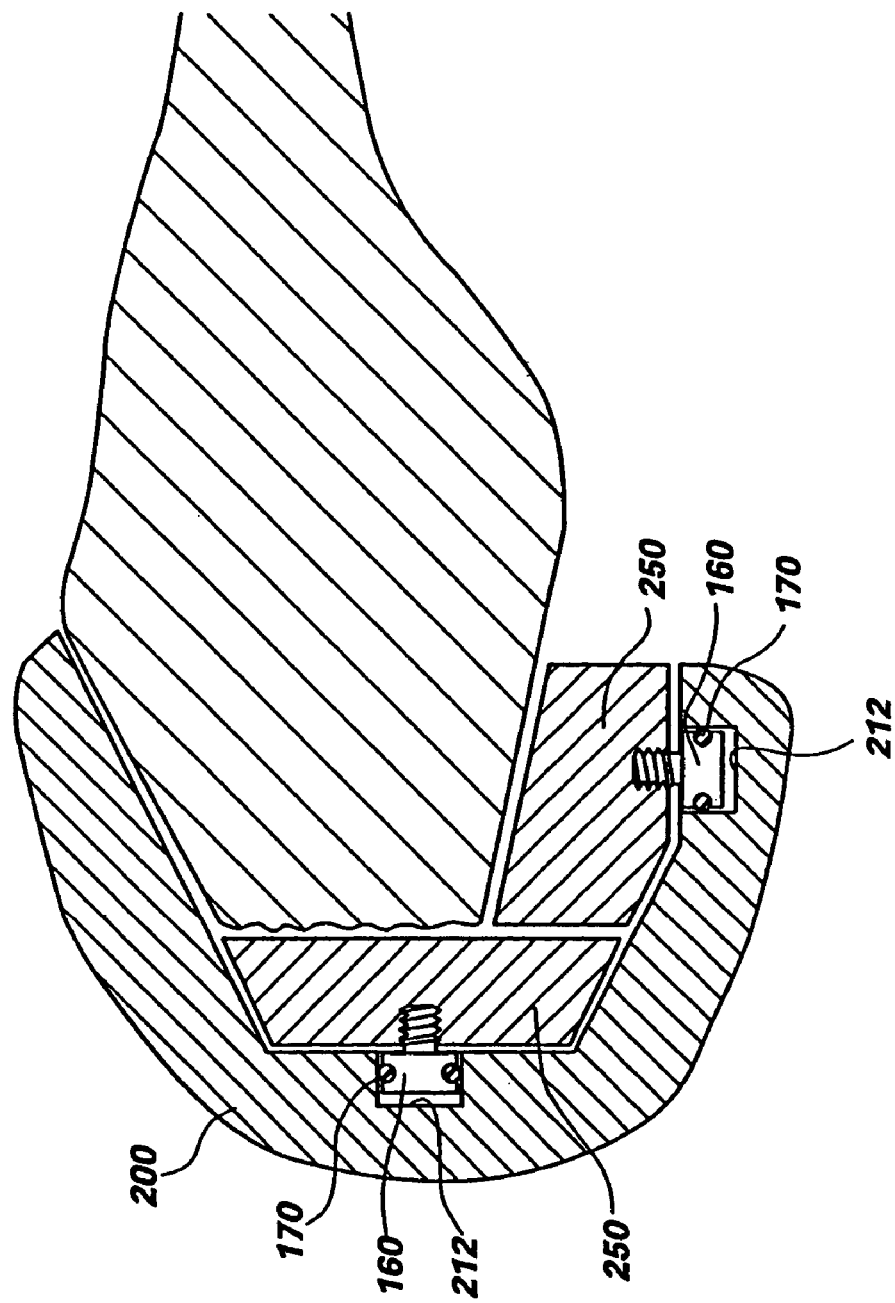

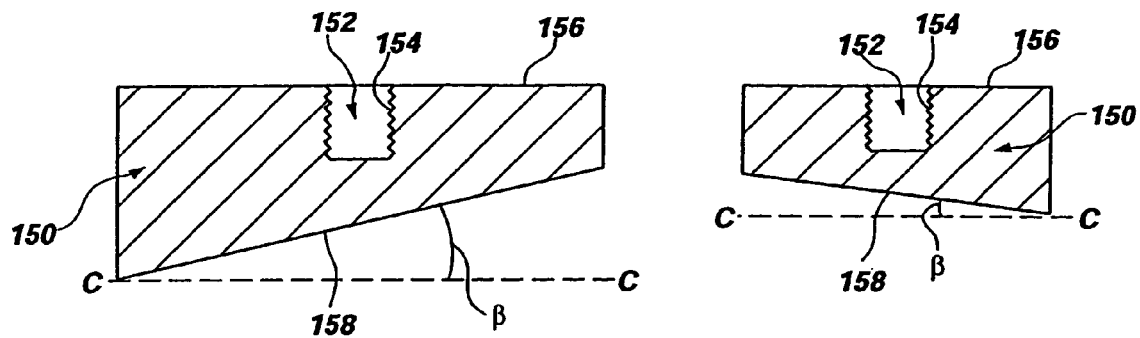
FIG. 10A
FIG. 10B
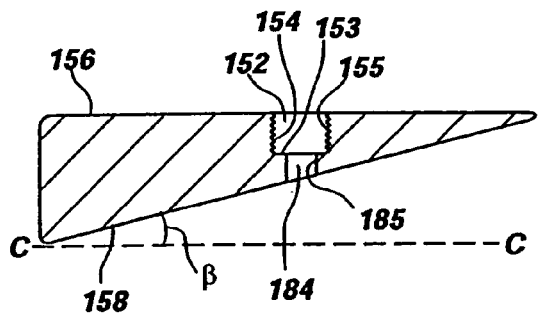
FIG. 10C
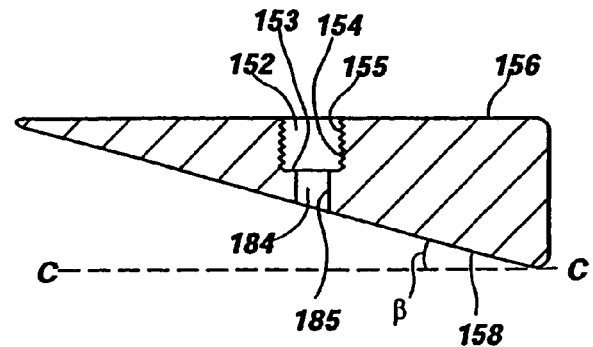
FIG. 10D

(Detail C)

(Detail B)

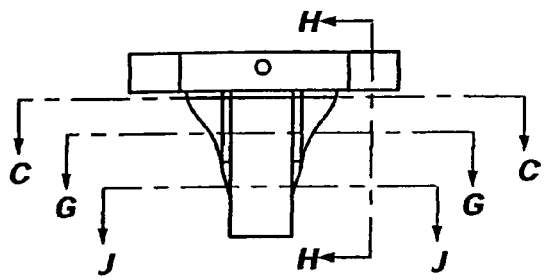
FIG. 31　　　　FIG. 32　　FIG. 33
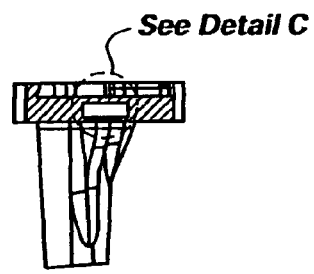
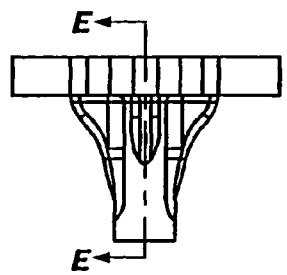
FIG. 34　　FIG. 35　　FIG. 36
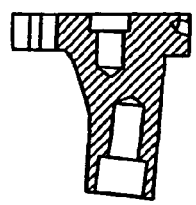
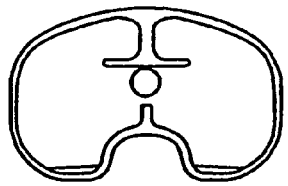
FIG. 37　　FIG. 38
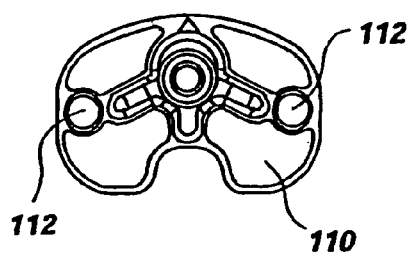
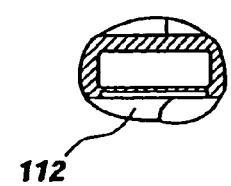
FIG. 39　　FIG. 40 (Detail C)

TIBIAL AUGMENT CONNECTOR

CROSS-REFERENCE TO RELATED APPLICATIONS

This application is a continuation of co-pending International Application PCT/US2004/001172, entitled "TIBIAL AUGMENT CONNECTOR," with an international filing date of Jan. 16, 2004, which claimed the benefit of U.S. Provisional Application No. 60/460,470, filed Apr. 2, 2003, entitled "TIBIAL AUGMENT CONNECTOR," and which also claimed the benefit of U.S. Provisional Application No. 60/464,870, filed Apr. 22, 2003, entitled "TIBIAL AUGMENT CONNECTOR," all of which are hereby incorporated by reference herein in their entireties, including but not limited to those portions that specifically appear hereinafter, the incorporation by reference being made with the following exception: In the event that any portion of any of the above-referenced applications is inconsistent with this application, this application supercedes said portion of the above-referenced applications.

STATEMENT REGARDING FEDERALLY SPONSORED RESEARCH OR DEVELOPMENT

Not Applicable.

BACKGROUND

1. The Field of the Invention

The present disclosure relates generally to orthopedic implants and devices, and more particularly, but not necessarily entirely, to an orthopedic implant, augment, and connector used in a revision surgery to rebuild a resected portion of bone that has been damaged, diseased, or otherwise diminished.

2. Description of Related Art

The knee joint is comprised essentially of four bones, the fibula, the tibia, the femur, and the patella or knee cap. The two major bones, namely the proximal portion of the tibia and the distal portion of the femur, articulate with one another forming the main articulation surface of the knee joint.

It is accepted practice in the orthopedic industry to replace a damaged or diseased knee joint with an artificial implant that acts a replacement knee joint. Following an original knee replacement surgery, there is potential for the tibia and femur to each experience damage or disease for various reasons, resulting in one or more of the prosthetic components that form the artificial knee implant to loosen from the patient's bone thereby causing that component to fail. When one or more of the prosthetic components fails, it may become necessary for an orthopedic surgeon to correct the deficiency in the artificial knee joint during a follow-up revision surgery.

As part of the revision surgery, a surgeon may have to remove the damaged or diseased bone, and may even need to replace one or more of the prosthetic components of the knee joint with a new prosthetic component or components. The reason for the replacement is commonly because either the individual components of the implant, or the bones themselves, have been damaged causing the failure. In either scenario, the damage to the components or bones will likely require the surgeon to resect additional bone from either the tibia or femur, or both, to remove the affected prosthetic components, and to replace those prosthetic components.

It will be appreciated that there is typically less bone for the surgeon to work with during the revision surgery as compared to the original surgery, since some amount of bone has been previously resected during the original surgery. Additional resection of the bone during the revision surgery further limits the amount of bone to which the new prosthetic components of the implant may be attached. At times, the surgeon may not have enough bone to adequately maintain an original joint line, which is formed between the tibial and femoral prosthetic components. It has become accepted practice in the orthopedic industry to provide augments or wedges to increase the height of the prosthetic components in order to help rebuild the resected portion of the bone, to thereby stabilize the revision components and maintain the joint line. It will be appreciated that these augments or wedges may be directly attached to the new femoral or tibial components. The augments not only function to increase the height of the implant to rebuild the joint line, where the original tibial and femoral prosthetic components articulated with one another in the original prosthetic knee joint, but also function to provide the necessary support for the new components of the revision implant. With the aid of the augments, the new revision components may be properly secured to the limited amount of bone present in the knee joint.

Attempts have been made in the art to provide an efficient connection between the augments and new prosthetic components. For example, U.S. Pat. No. 5,370,693 (granted Dec. 6, 1994 to Kelman et al.) discloses an implant having an augment configured to be attached to a surface of the implant by bone cement to compensate for bone loss. The augment is formed to include an aperture defined by an inner wall. Kelman et al. also discloses a peg that is configured to engage the inner wall of the aperture in the augment thereby retaining the augment in a spaced apart relation relative to the implant to permit the implant to be installed onto the bone before the bone cement cures. This device is characterized by several disadvantages, including the need to use bone cement to attach the augment to the implant, which may permit the augment to loosen over time from the implant.

There are several other augment or wedge devices known in the art, such as that disclosed in U.S. Pat. No. 5,458,637 (granted Oct. 17, 1995 to Hayes). This patent reference discloses an augmentation block that includes an attachment mechanism that uses a button and a key hole shaped opening in a tibial tray component to attach the augmentation block to the tibial tray component. This device is disadvantageous because the button locks to the key hole through a top surface of the implant, which key hole is formed completely through the tibial tray. Such a hole formed through the tibial tray may disadvantageously introduce unwanted wear debris pathways into the implant.

It is noteworthy that none of the prior art known to applicant provides a locking mechanism for securing an augment member to a tibial tray component or a femoral component that locks via an interference snap-fit, without fastening the augment member to a through hole extending through a top surface of the tibial tray component or femoral component. There is a long felt, but unmet, need for an augment member that may be securely locked to the implant without introducing unwanted wear debris pathways. Applicant has thus conceived of a locking feature that is simple in design and manufacture, and that may limit, or even eliminate, wear debris pathways.

The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 9 is a side, cross-sectional view of an alternative embodiment of the present disclosure, made in accordance with the principles of the present disclosure;

FIGS. 10A-10D are side views of alternative embodiments of the augment members of the present disclosure;

FIG. 31 is another front view of the revision tibial tray of FIG. 17, made in accordance with the principles of the present disclosure;

FIG. 32 is a cross-sectional view taken along the line C-C of FIG. 31;

FIG. 33 is a cross-sectional view taken along the line G-G of FIG. 31;

FIG. 34 is a cross-sectional view taken along the line H-H of FIG. 31;

FIG. 35 is a cross-sectional view taken along the line J-J of FIG. 31;

FIG. 36 is a back view of the revision tibial tray of FIG. 17, made in accordance with the principles of the present disclosure;

FIG. 37 is a cross-sectional view taken along the line E-E of FIG. 36;

FIG. 38 is another top view of the revision tibial tray of the present disclosure;

FIG. 39 is another bottom view of the revision tibial tray of the present disclosure; and FIG. 40 is a detail view referred to as Detail C in FIG. 34.

DETAILED DESCRIPTION

Figure 1:
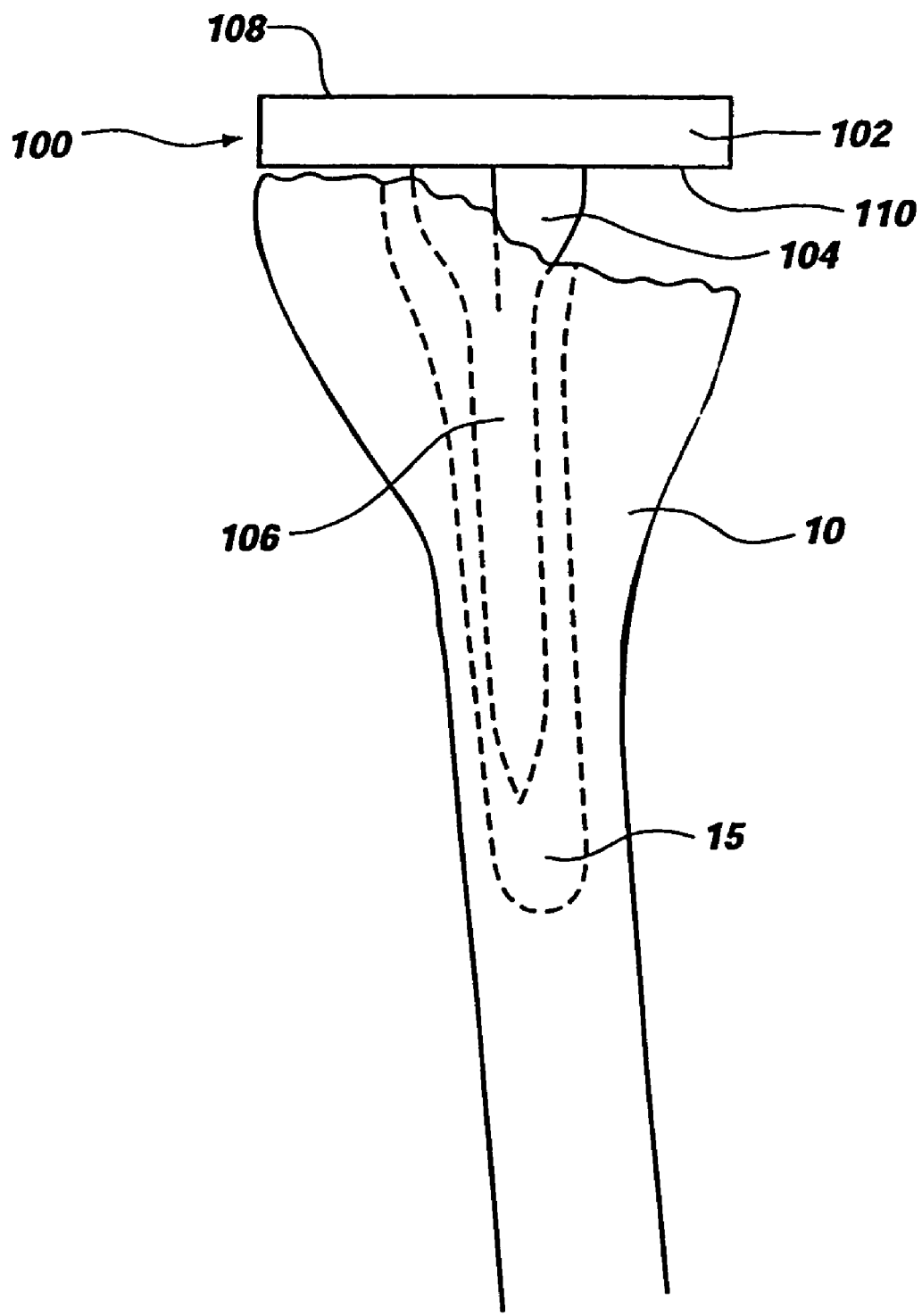
FIG. 1 is a side, representational view of a damaged tibial bone with a tibial implant located therein.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the device of the present disclosure is described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the claims and equivalents thereof.

The publications and other reference materials referred to herein to describe the background of the disclosure, and to provide additional detail regarding its practice, are hereby incorporated by reference herein in their entireties, with the following exception: In the event that any portion of said reference materials is inconsistent with this application, this application supercedes said portion of said reference materials. The reference materials discussed herein are provided solely for their disclosure prior to the filing date of the present application. Nothing herein is to be construed as a suggestion or admission that the inventors are not entitled to antedate such disclosure by virtue of prior disclosure, or to distinguish the present disclosure from the subject matter disclosed in the reference materials.

It will be appreciated that the dimensions and tolerances as detailed in the figures are for exemplary and illustrative purposes only, and such dimensions and tolerances are not limiting of the scope of the claims, except for any claims in which such dimensions or tolerances are expressly included.

It should be noted that, as used in this specification, the singular forms "a," "an," and "the" include plural referents unless the context clearly dictates otherwise.

In describing the present disclosure, the following terminology will be used in accordance with the definition(s) set out below.

As used herein, the terms "comprising," "including," "containing," "characterized by," and grammatical equivalents thereof are inclusive or open-ended terms that do not exclude additional, unrecited elements or method steps.

It will be appreciated that the principles of the present disclosure may be applied to various joints in a human body, and is not limited to a specific joint. However, it should be noted that the principles of the present disclosure will be discussed and illustrated specifically in relation to a knee joint, for exemplary purposes only. It is to be understood that applicant does not intend the discussion and illustration that follows to limit the scope of the present disclosure to the tibial or femoral component of a prosthetic knee joint, or even to the knee joint generally, as the principles of the present disclosure may be applied equally to other implants, and to other joints of the human body.

The present disclosure may be directed to an orthopedic implant and device that may be used in revision knee surgeries as a connection between part of a prosthetic knee implant and an augment member 150. It will be appreciated that the term "implant" as used herein may refer collectively to the components that make up the entire knee replacement, or the term "implant" as used herein may refer to each individual component of the knee replacement. Specifically, FIG. 1 illustrates a damaged or diseased proximal tibia 10 having a tibial component 100, sometimes referred to herein as a tibial implant or implant member, located within a canal 15 of the tibial bone 10. It will be appreciated that the tibial component 100, as illustrated in FIG. 1, may not be properly maintained within such a damaged or diseased bone, and may ultimately loosen from the bone causing the component 100 to fail. The present disclosure is directed to correcting the above, or similar, scenario.

At times, the damage to the tibial bone 10 may be so severe that a revision surgery becomes necessary. It will be appreciated that revision surgeries are often difficult to perform for various reasons. One reason for the difficulty is that less bone may be available for the prosthetic components of the implant (whether tibial or femoral) to contact and to be implanted into, due, at least in part, to the previous resection of the bone. As illustrated in FIG. 1, the component 100 may not be properly supported by the bone. Another factor that reduces the amount of bone present for the component to be installed into during the revision surgery may be due, at least in part, to the amount of bone that has been damaged or diseased since the original surgery. During the revision surgery it is sometimes necessary for a surgeon to further resect the bone in order to remove the damaged or disease bone.

During the revision surgery, it may be advantageous for the surgeon to rebuild at least a portion of the bone that has been resected in order to provide the necessary joint line between the femur and tibia, such that a femoral component 200 of the prosthetic knee joint may fit, articulate, and work properly with the tibial component 100. It will be appreciated that the joint line may be described as the location in the prosthetic knee joint where the original tibial and femoral prosthetic components articulated with one another. Therefore, it has become standard or accepted procedure in the orthopedic industry to provide at least one augment member 150 to rebuild at least a portion of the bone that was previously resected such that the implant may be securely positioned within the bone to provide the necessary joint line.

Reference will now be made to FIGS. 1-12 collectively, with specific reference made to particular drawings when specified below, and with the understanding that similar reference numerals will be used to indicate similar structure for each component.

Figure 2:
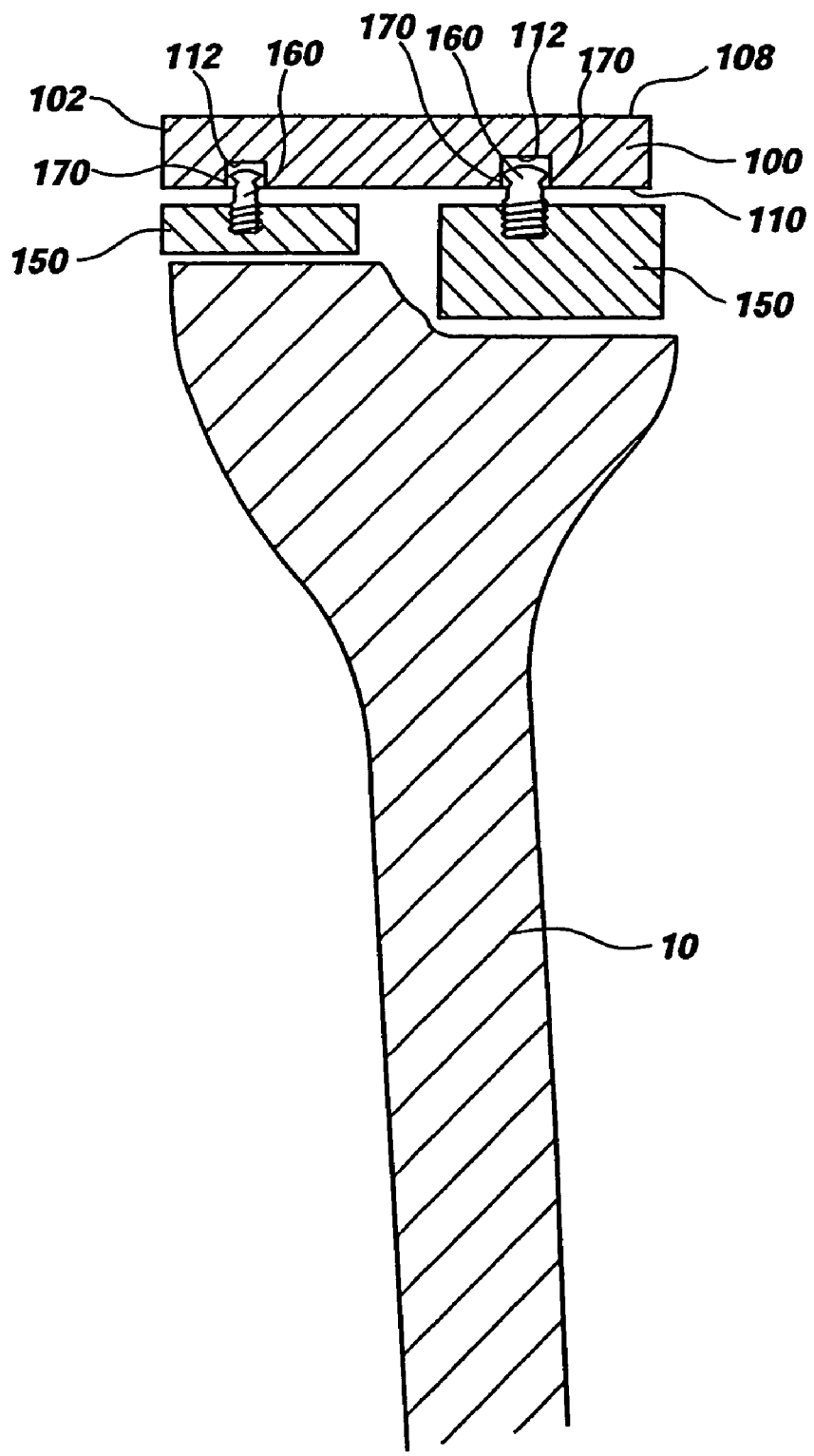
FIG. 2 is a side, cross-sectional view of a resected tibial bone, with a representation of a tibial tray and a plurality of augment members attached thereto, made in accordance with the principles of the present disclosure.

The concept of one embodiment of the present disclosure is illustrated in FIG. 2, and may be directed to the connection between the tibial component 100 and at least one augment member 150. Generally, the device of the present disclosure may comprise the tibial component 100, the at least one augment member 150, at least one fastener 160, and at least one connector 170. It will be appreciated that other components, besides the tibial component 100, may be utilized by the present disclosure. For example, the present disclosure may be utilized in conjunction with a femoral component 200, sometimes referred to herein as a femoral implant or implant member. It will be appreciated that the tibial component 100 will be particularly described herein as exemplary of the principles of the present disclosure, even though the principles of the present disclosure may be equally applied to other components, for example the femoral component 200.

It will be appreciated that the components of the present disclosure may be manufactured from any biocompatibly suitable material, including titanium or titanium alloys. For example, the above components may be manufactured from commercially pure (CP) titanium metal or a suitable alloy thereof (e.g. 90% Ti, 6% Al, 4% V). In addition, the above components may be manufactured from other suitable biocompatible materials known, or which may become known in the future, in the art possessing similar biocompatible qualities and characteristics as titanium or titanium alloys.

Referring to FIGS. 1 and 2, it will be appreciated that the tibial component 100 may generally comprise a tibial tray 102, a keel 104, and a stem 106. The tibial tray 102 may comprise a top surface 108 and a bottom surface 110. The keel 104 may extend beneath the bottom surface 110 of the tibial tray 102, and may be configured as a modular piece or as an integral piece with respect to the tibial tray 102. The stem 106 of the tibial component 100 may extend beneath the keel 104 and may be dimensioned to fit within the canal 15 of the tibial bone 10, and configured to provide stabilization and support to the component 100 within the tibial bone 10. It will be appreciated that the stem 106 may be designed as a modular piece or as an integral piece with respect to the keel 104 or tibial tray 102.

Figure 21:
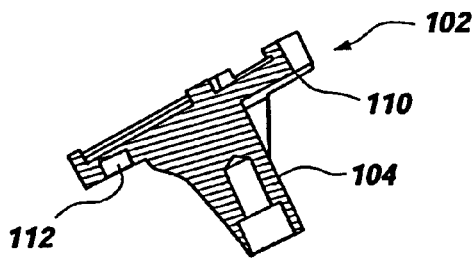
FIG. 21 is a cross-sectional view taken along the line A-A of FIG. 20.
Figure 23:
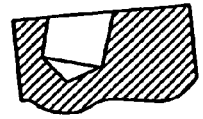
FIG. 23 is a detail view referred to as detail C in FIG. 22.
Figure 22:
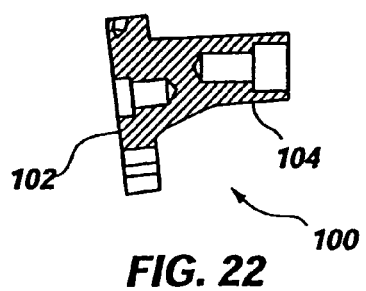
FIG. 22 is a cross-sectional view taken along the line B-B of FIG. 20.
Figure 20:
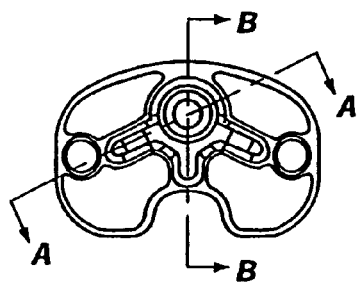
FIG. 20 is a bottom view of the revision tibial tray of FIG. 17, made in accordance with the principles of the present disclosure.
Figure 24:
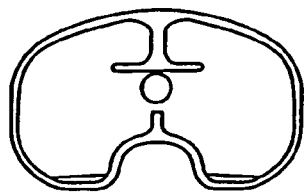
FIG. 24 is a top view of the revision tibial tray of FIG. 17, made in accordance with the principles of the present disclosure.
Figure 26:
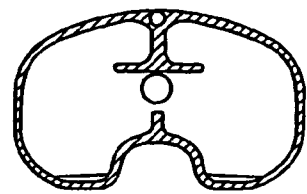
FIG. 26 is a cross-sectional view taken along the line D-D of FIG. 25.
Figure 27:
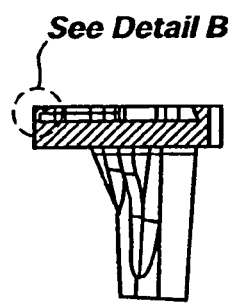
FIG. 27 is a cross-sectional view taken along the line F-F of FIG. 25.
Figure 25:
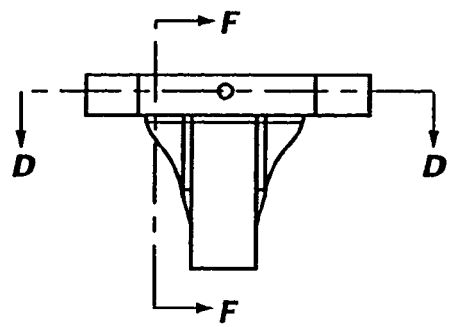
FIG. 25 is a front view of the revision tibial tray of FIG. 17, made in accordance with the principles of the present disclosure.
Figure 28:
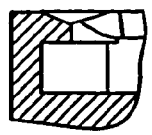
FIG. 28 is a detail view referred to as Detail B in FIG. 27.
Figure 29:
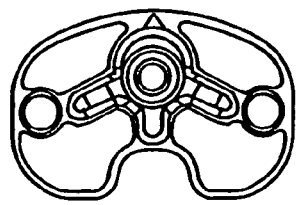
FIG. 29 is a bottom view of the revision tibial tray of FIG. 17, made in accordance with the principles of the present disclosure.
Figure 30:
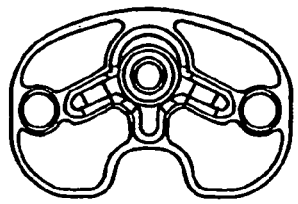
FIG. 30 is another bottom view of the revision tibial tray of FIG. 17, made in accordance with the principles of the present disclosure.

Referring collectively now to FIGS. 16-40, and particularly to FIGS. 21 and 40, wherein a revision tibial tray 102 is illustrated. Referring specifically to FIG. 21, it will be appreciated that the revision tibial tray 102 of the present disclosure may include at least one recess 112 formed in the bottom surface 110. The at least one recess 112 may be formed as illustrated in FIG. 21. The at least one recess is further detailed in FIGS. 40 and 3B, both of which are detailed views of the at least one recess 112.

Figure 3:
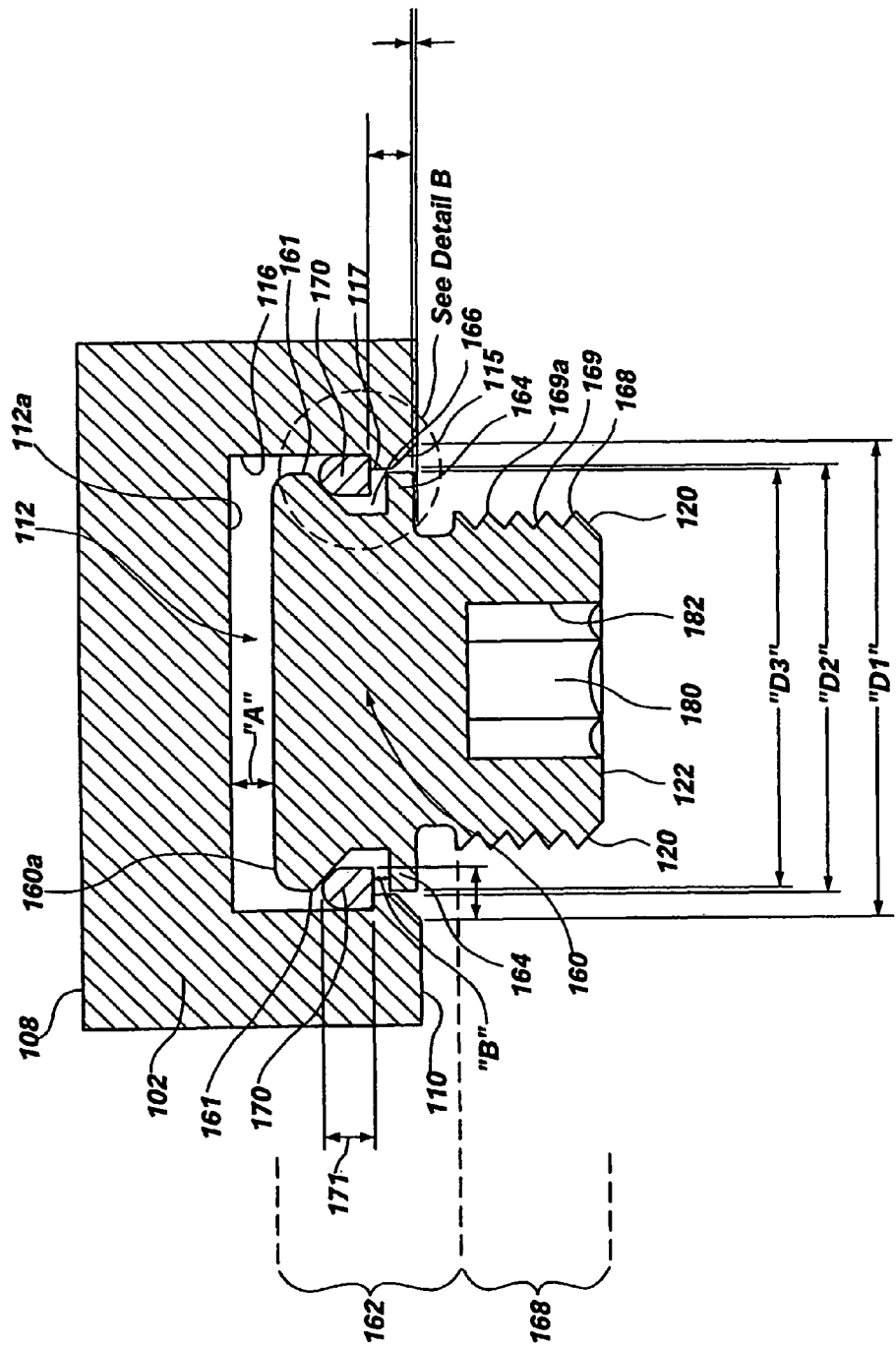
FIG. 3 is a side, cross-sectional view of a snap-fit connection between the tibial tray, a fastener, and a connector, made in accordance with the principles of the present disclosure.
Figure 3A:
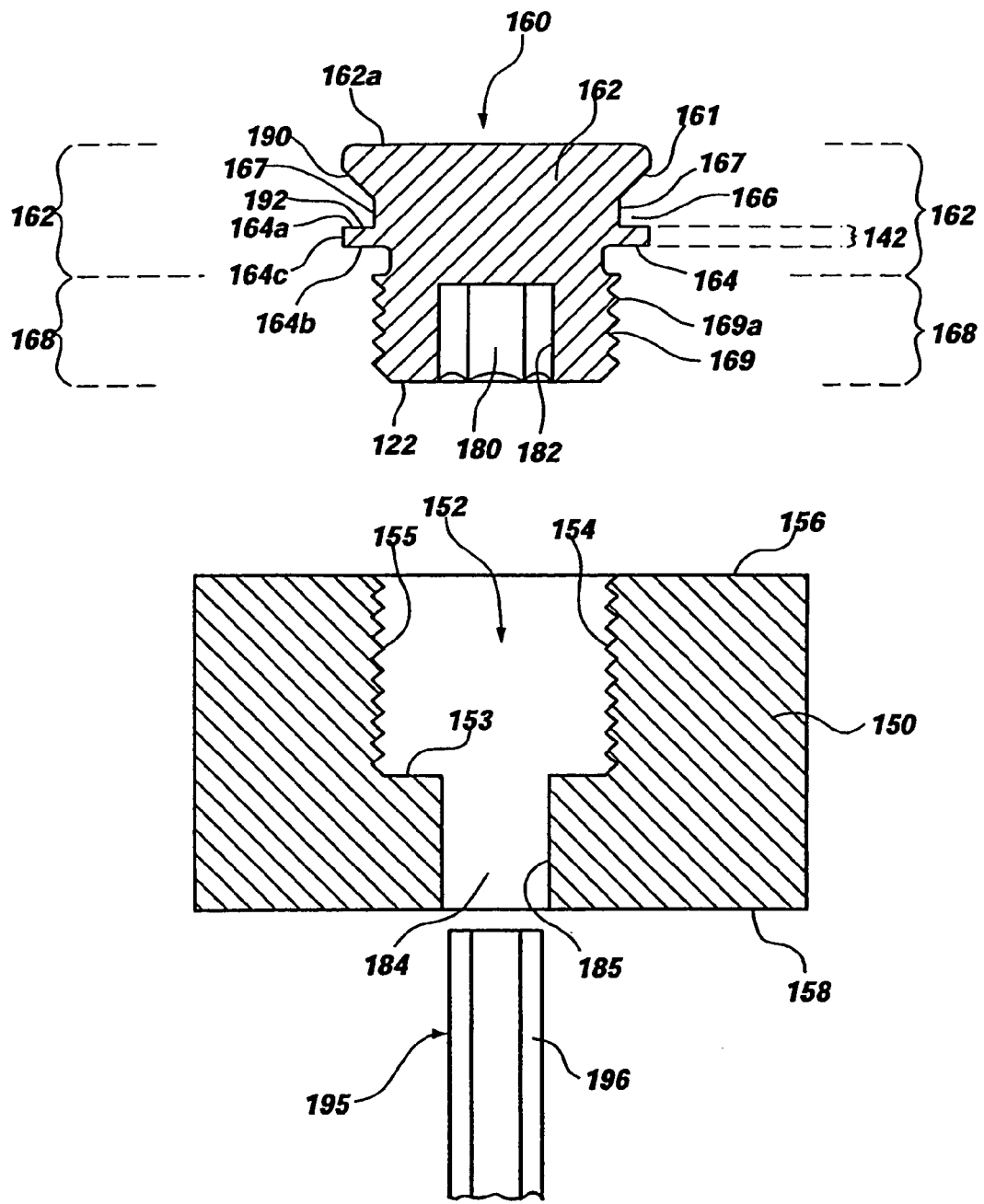
FIG. 3A is a side, cross-sectional exploded view of the fastener and the augment member, made in accordance with the principles of the present disclosure.
Figure 3B:
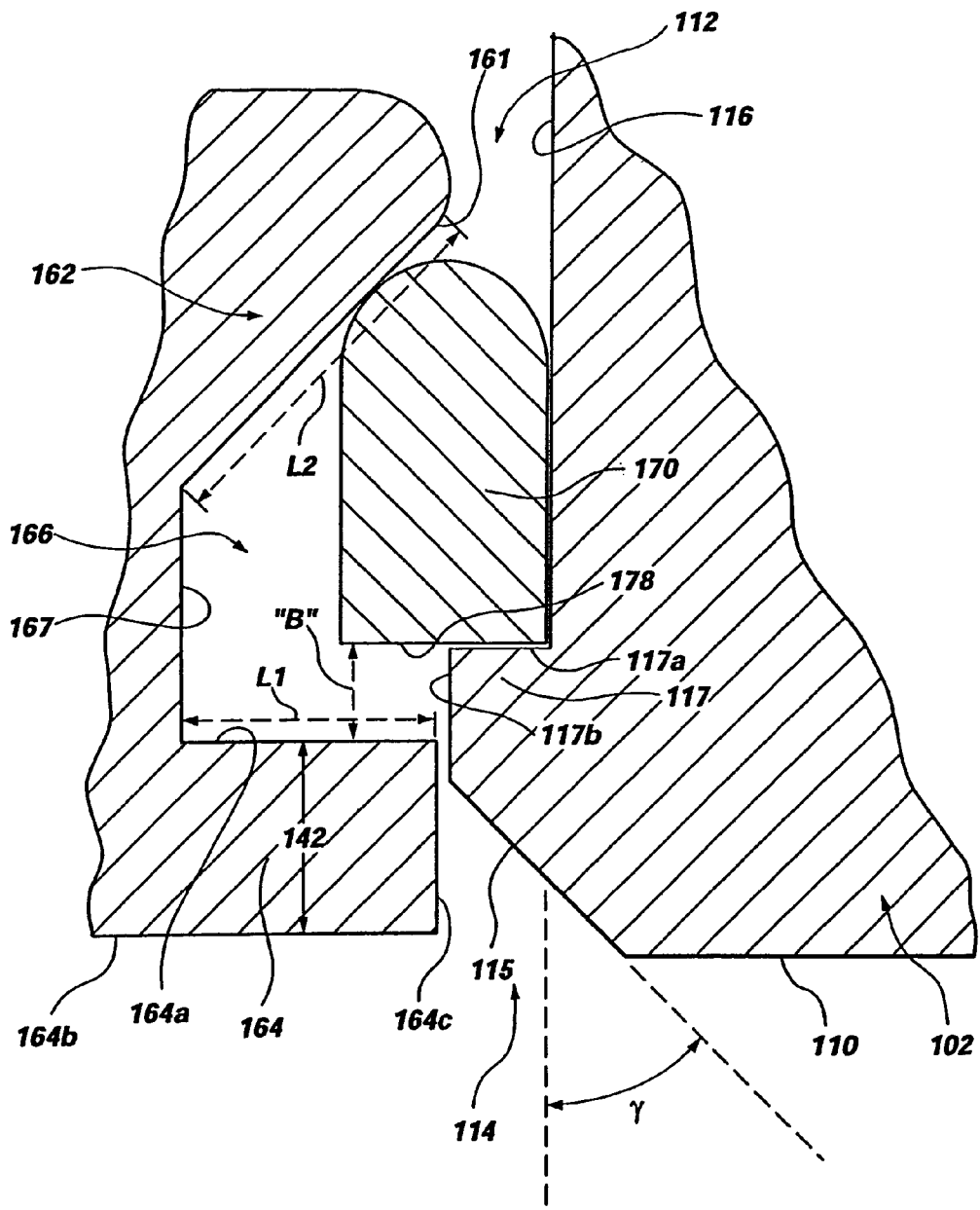
FIG. 3B is a enlarged cross-sectional view of detail B of FIG. 3.
Figure 15:
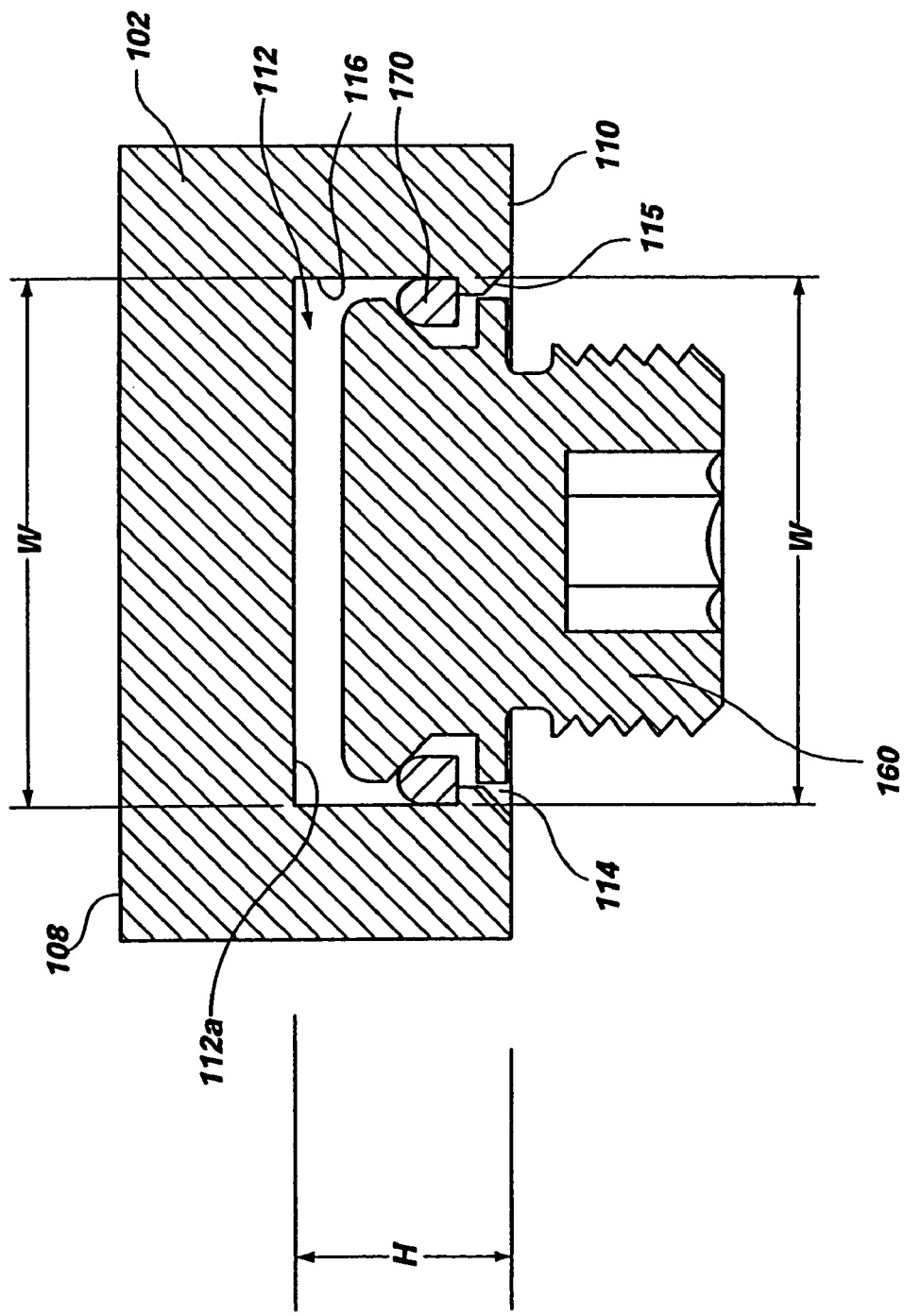
FIG. 15 is a side, cross-sectional view of the tibial tray, fastener, and connector, made in accordance with the principles of the present disclosure.
Figure 16:
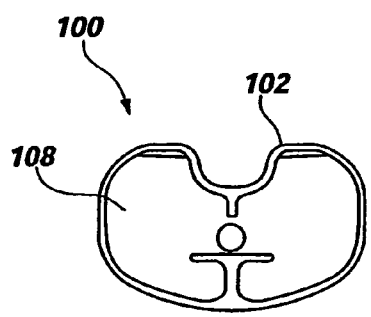
FIG. 16 is a top view of a revision tibial tray, made in accordance with the principles of the present disclosure.
Figure 17:
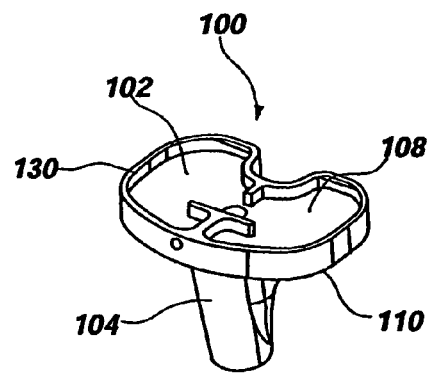
FIG. 17 is a perspective view of the revision tibial tray of FIG. 16, made in accordance with the principles of the present disclosure.
Figure 18:
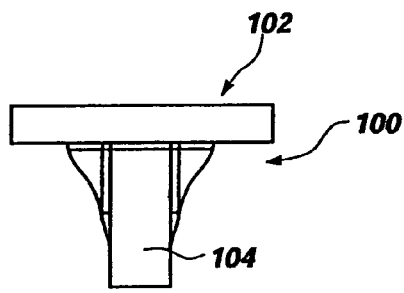
FIG. 18 is a front view of the revision tibial tray of FIG. 17, made in accordance with the principles of the present disclosure.
Figure 19:
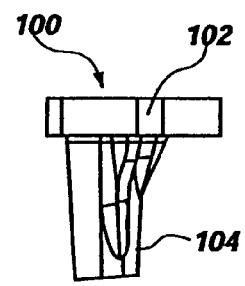
FIG. 19 is a side view of the revision tibial tray of FIG. 17, made in accordance with the principles of the present disclosure.

Referring now to FIGS. 3 and 3B, the tibial component 100 is illustrated with the at least one recess 112 formed in the bottom surface 110 of the tibial tray 102. It will be appreciated that each recess 112 may be characterized by the absence of a through hole extending from the top surface 108 to the bottom surface 110 of the tibial tray 102. Each recess 112 may comprise an opening 114 accessible from the bottom surface 110 of the tibial component 100, and each recess 112 may be defined by a wall 116. It will be appreciated that the wall 116 of the recess 112 may be characterized by the absence of threads. Additionally, it will be appreciated that each recess 112 may comprise a width, which may be defined as the measurement from a first point located on the wall 116 of the recess 112 to a second point located opposite the first point on the wall 116 of the recess 112, represented by the letter "W." Each recess 112 may further comprise a height, which may be defined as the measurement from the opening 114 of the recess 112 to an upper surface 112a of said recess 112, represented by the letter "H" (illustrated best in FIG. 15).

Each recess 112 may be dimensioned, for example, such that the height dimension H may be within a range from about 15% to about 100% of the width dimension W. For example, the height H of the recess 112 may be within a range from about 20% to about 80% of the width W of the recess, or a range from about 25% to about 75%, or a range from about 33% to about 67%. More specifically, the height H of the recess 112 may be within a range from about 40% to about 60% of the width W of the recess 112. It will be appreciated that the relationship between the height H and the width W of the recess 112 may be between the above stated ranges without departing from the scope of the present disclosure.

It will be appreciated that the at least one recess 112 may be configured and arranged as part of the connection between the tibial tray 102 and the at least one augment member 150. It will be appreciated that the at least one recess 112 may correspond in number with the number of augment members 150 utilized per component 100, such that when more than one augment member 150 is utilized by the present disclosure, more than one recess 112 may also be utilized in the corresponding component 100.

Additionally, more than one recess 112, and consequently more than one fastener 160 and more than one connector 170, may be used to connect one augment member 150 to the tibial tray 102. It will be appreciated that it may be advantageous to utilize more than one recess 112 per augment member 150 to more securely attach the augment member 150 to the tibial tray 102.

As illustrated in FIGS. 3 and 3B, the opening 114 may comprise a dimension "D1" that may be defined as the distance between two points of the opening 114 that are directly opposite each other on the bottom surface 110 of the tibial tray 102. A surface 115 may be situated proximally with respect to the opening 114, and may define part of the recess 112, and may also protrude slightly beyond the wall 116 into the recess 112 of the tibial tray 102. The surface 115 may taper at an angle γ, with respect to the wall 116 of the recess 112, in a proximal-to-distal direction. The angle γ of the surface 115 may be within a range from about thirty degrees to about sixty degrees. For example, applicant has found that the angle γ may be within a range from about thirty-five degrees to about fifty-five degrees, and more specifically the angle γ may be within a range from about forty degrees to about fifty degrees, such as forty-five degrees, and each of the above angles have been found to be advantageous. It will be appreciated that the surface 115 may extend beyond the width dimension W of the recess 112, such that the width D1 of the opening 114 may be larger than the width dimension W of the recess 112.

It will be appreciated that the surface 115 may operate as a lead-in chamfer and for contacting the connector 170 in such a manner so as to provide a compression force on the connector 170, as a head portion 162 of the fastener 160 enters through the opening 114 of the recess 112, thereby allowing at least a part of the head portion 162 and the connector 170 to be seated within the recess 112. It will be appreciated that the tapered configuration and shape of the surface 115, operating as the lead-in chamfer, may aid in compressing the connector 170 into a multi-surface recess 166, as the head portion 162 is positioned within the recess 112. It will likewise be appreciated that the surface 115 may also permit the head portion 162 to effortlessly enter through the opening 114 and into the recess 112 due, at least in part, to the tapering of the surface 115, which may further operate to widen the opening 114 into the recess 112.

It will be appreciated that the fastener 160 may be configured and dimensioned to snap-fit into the recess 112 of the tibial tray 102. More specifically, as the head portion 162 of the fastener 160 enters through the opening 114 of the recess 112, the connector 170, which may be pre-installed onto the fastener 160, may contact and engage the surface 115. As additional upward force is applied to the fastener 160, the connector 170 may be forced farther into the multi-surface recess 166 of the fastener 160 as at least a portion of the head 162 and the connector 170 pass by the surface 115. After the connector 170 and part of the head portion 162 of fastener 160 passes the surface 115, the connector 170 and the head portion 162 snap into position within the recess 112.

It will be appreciated that a ledge 117 may be formed within the recess 112 and may comprise a top surface 117a and a side surface 117b, and the tapered surface 115 may be used to form a bottom portion of the ledge 117. As illustrated in FIG. 3B, the ledge 117 may be a protrusion, and may protrude slightly into the recess 112 away from the wall 116. The top surface 117a may be configured and dimensioned to engage a bottom surface 178 of the connector 170, such that the connector 170 may be retained within the recess 112 in an interference fit with the ledge 117 and the wall 116 of the recess 112. The top surface 117a of the ledge 117 may be orthogonally formed with respect to the wall 116 of the recess 112, although other geometric configurations may also be used such that the connector 170 may be retained within the recess 112. It will be appreciated that once the head portion 162 and the connector 170 are positioned within the recess 112, an interference snap-fit may be formed between the wall 116 of the recess 112, a frusto-conical surface 161 of the head portion 162 of the fastener 160, and the top surface 117a of the ledge 117, to thereby retain the fastener 160 within the recess 112 of the tibial tray 102.

It will be recognized that a significant amount of the total force exerted on the ledge 117 may be distributed through the component 100 to the augment member 150, when the augment member 150 is cinched up tightly against the bottom surface 110 of the component 100. Accordingly, it will be appreciated that a thickness of the ledge 117 may be modified to increase or decrease the strength of the ledge 117. As the thickness of the ledge 117 is increased, the ledge 117 may be strengthened. Conversely, as the thickness of the ledge 117 is decreased, the ledge 117 may be weakened.

It will likewise be appreciated that the dimensions of the ledge 117, i.e. the height and width, determine how far the ledge 117 protrudes into the recess 112, and may affect the dynamics of the relationship of the connector 170 to the multi-surface recess 166. The ledge 117 may protrude from the wall 116 into the recess 112 within a range from about 1% to about 10% of the width W of the recess 112, and more particularly within a range from about 2% to about 8%, and even more particularly within a range from about 3% to about 5%. Conversely, the height of the ledge 117 may be within a range from about 5% to about 20% of the height dimension H of the recess 112. More particularly, the height of the ledge 117 may be within a range from about 10% to about 15%, and even more particularly within a range from about 11% to about 13% of the height dimension H of the recess 112.

It will be appreciated that the at least one augment member 150 of the present disclosure may be configured and dimensioned to attach directly to the recess 112 formed in the bottom surface 110 of the tibial tray 102 by way of the interference snap-fit referred to above. Each augment member 150 may be attached to the tibial tray 102 at a single connection or attachment site, or at multiple connection or attachment sites without departing from the scope of the present disclosure. It will be appreciated that attachment at multiple connection sites may provide additional stabilization and a strengthened connection between the augment member 150 and the tibial tray 102. Accordingly, if multiple connection sites are utilized by the present disclosure, there may be multiple recesses 112 provided in the tibial tray 102, or other component, as described above.

Referring now to FIGS. 3A, and 10A-10D, it will be appreciated that each augment member 150 may comprise a top surface 156, a bottom surface 158, and a recess 152, sometimes referred to herein as a cavity. The recess 152 may be defined by a sidewall 154 that may be configured to matingly engage a body member 168 of the fastener 160. Each augment member 150 may further comprise a through passage 184, that may be configured and dimensioned to permit the passage of a surgical tool 195 therethrough. It will be appreciated that each of the augment members 150 may be attached to the body member 168 of the fastener 160 to thereby secure each of the augment members 150 to the tibial tray 102.

Each fastener 160, also referred to herein as a means for connecting the augment member 150 to the component or implant 100 or 200, may comprise the head portion 162 and the body member 168, referred to above. The head portion 162 may comprise a retention lip 164 and the multi-surface recess 166. It will be appreciated that at least one fastener 160, and its component parts, may be used to attach the at least one augment member 150 to the bottom surface 110 of the tibial tray 102. Multiple fasteners 160 and connectors 170 may be used by the present disclosure, which may snap-fit into multiple recesses 112, when multiple connection sites between one augment member 150 and the tibial tray 102 are utilized. Additionally, one fastener 160 and one connector 170 may be utilized to form the interference snap-fit, and may be used in conjunction with other attachment mechanisms to secure the augment member 150 to the tibial tray 102.

Figure 13:
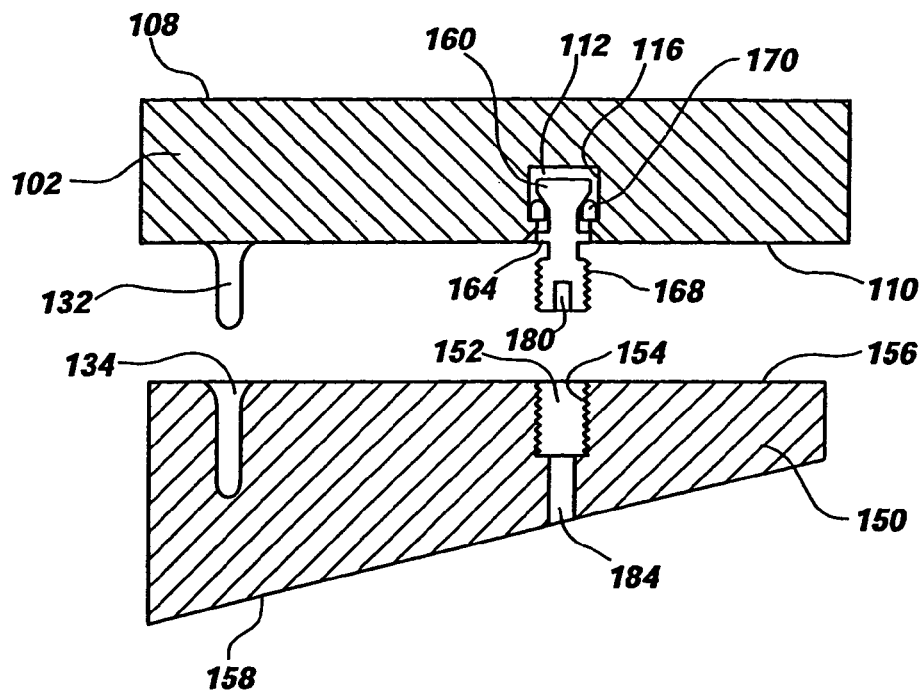
FIGS. 13-13A are side, cross-sectional views of alternative embodiments of an additional connecting mechanism, made in accordance with the principles of the present disclosure.
Figure 13A:
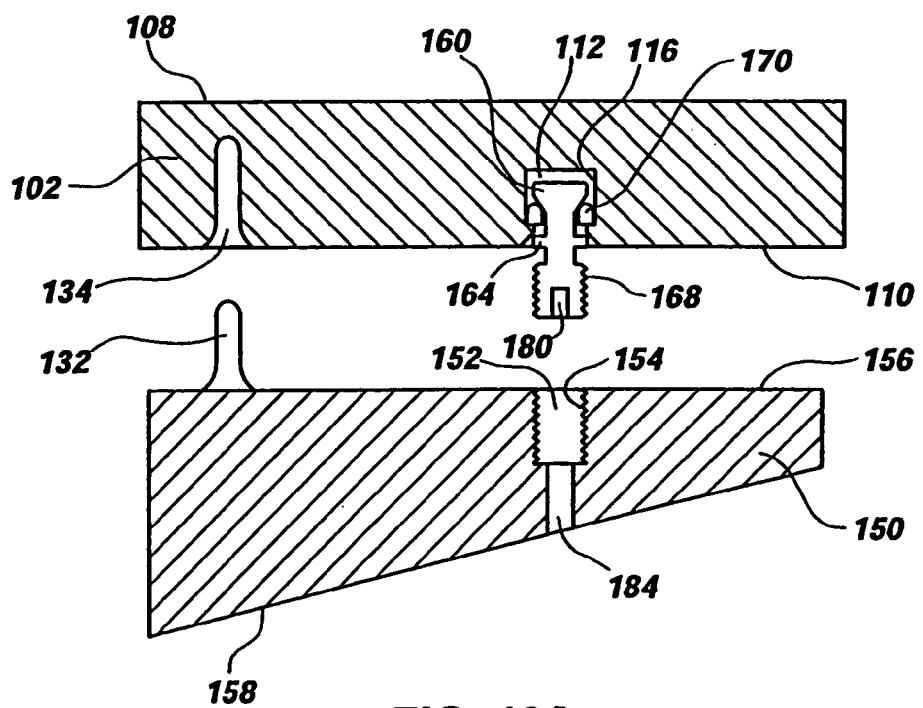
Figure 14:
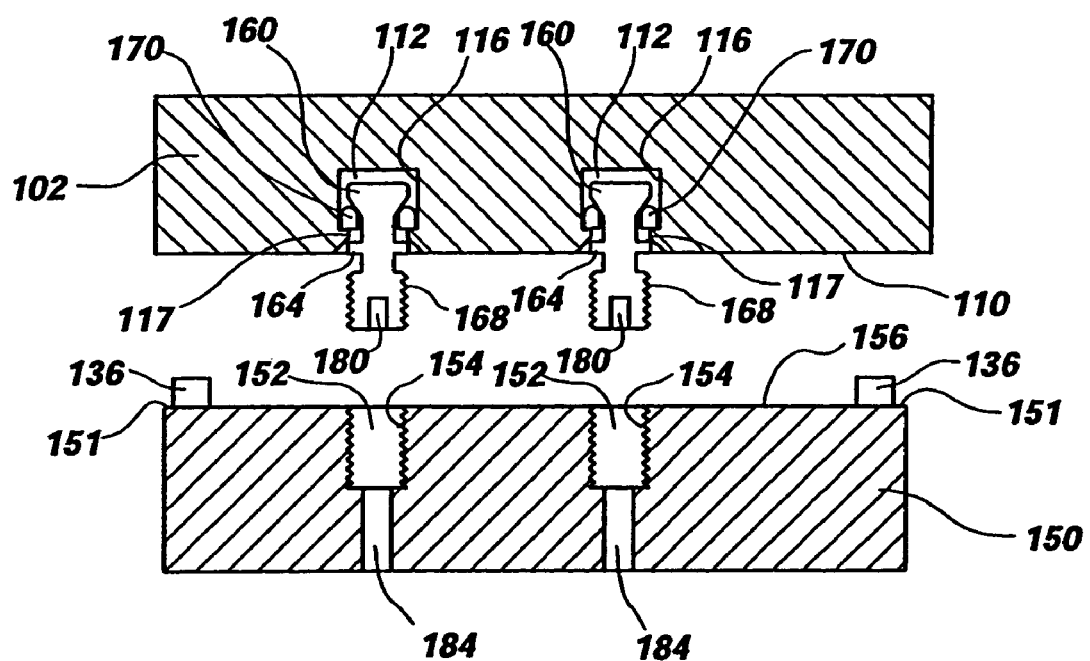
FIG. 14 is a side, cross-sectional view of an alternative embodiment of another connecting mechanism, made in accordance with the principles of the present disclosure.

For example, an interference snap-fit connection, described above, between the frusto-conical surface 161 of the fastener 160, the connector 170, the ledge 117 and the wall 116 of the recess 112, may be used in conjunction with: (1) a lip formed on at least one side of the augment member 150 to attach the augment member 150 to a lip portion 130 of the tibial tray 102; for example, the lip may be formed on a posterior side 157 of the augment member 150 and may attach itself to the lip portion 130 formed on the top surface 108 of the tibial tray 102 (illustrated best in FIG. 17); (2) an attachment peg 132, also referred to herein as a stabilizing peg, formed on either the bottom surface 110 of the tibial tray 102, or the top surface 156 of the augment member 150, and a corresponding recess 134 formed in the opposite component, such that an attachment between the attachment peg 132 and the corresponding recess 134 may be formed (illustrated best in FIGS. 13 and 13A); or (3) at least one rail 136 connected on the top surface 156 of the augment member 150 to secure the position of the augment member 150 within a pocket of cement located on the bottom surface 110 of the tibial tray 102, such that the at least one rail 136 may operate as an anti-rotation mechanism (illustrated best in FIG. 14). It will be appreciated that the at least one rail 136 may be located on the top surface 156 and parallel to an outside edge 151 of the augment member 150. The at least one rail 136 may comprise two rails 136, both of which may be located parallel to the outside edge 151 of the augment member. It will be appreciated that the at least one rail 136 may also be more than two rails, without departing from the scope of the present disclosure.

Referring specifically to FIG. 3, wherein a side, cross-sectional view of the tibial tray 102, the fastener 160 and the connector 170 are illustrated. As illustrated, the tibial tray 102 may comprise the at least one recess 112 referred to above. It should be noted that while the tibial tray 102 of the present disclosure may comprise the recess 112, the tibial tray 102, or other component, may be characterized by the absence of a through hole for connecting the augment member 150 to the tibial tray 102. The absence of a through hole in the tibial tray 102 may be an advantage in the present disclosure because the tibial tray 102 may not introduce a wear debris pathway, and therefore the generation of wear debris pathways may be reduced, or even eliminated. It will also be appreciated that any tibial component 100 may be utilized by the present disclosure as long as the tibial component 100 comprises the at least one recess 112 referred to above.

It will be appreciated that a dimension "D2" of the recess 112, at its narrowest section, may be slightly larger than a dimension "D3" at the widest section of the head portion 162 of the fastener 160, such that the head portion 162 may be positioned and located within the recess 112 of the tibial tray 102. As used herein, the dimension D2 may refer to the distance between two points that are directly opposite one another on the side surface 117b of the ledge 117 of the recess 112. Whereas the dimension D3 may refer to the largest distance between two points that are directly opposite one another on the head portion 162 of the fastener 160. It will further be appreciated that the dimension D2 of the recess 112, while slightly larger than the dimension D3 of the head portion 162, may not be so large that the connector 170 cannot form an interference fit with the ledge 117 and the wall 116 of the recess 112, and the frusto-conical surface 161 of the multi-surface recess 166 of the fastener 160. Additionally, the dimension D1 of the opening 114 may be larger than both dimension D2 of the recess 112 and dimension D3 of the head portion 162.

It will be appreciated that the use of threads in a hole, cavity, or recess of an implant, such as the tibial component 100 or femoral component 200, may lead to the occurrence of stress risers within the component, which disadvantageously have potential to cause the component to corrode and/or fracture prematurely. Stress risers may occur at the point or points where sharp edges of the threads are located within the hole, cavity, or recess of the component, because the sharp edges of the threads create stress paths that concentrate loads in those areas. Stress risers may operate to distribute an excess amount of force at the location of the threads. Accordingly, it will be appreciated that the present disclosure may reduce or even eliminate the occurrence of stress risers within the component 100 by manufacturing the wall 116 of the recess 112 without utilizing threads, such that no sharp edges or corners may be introduced into the component 100. Accordingly, applicant has conceived of a unique design for connecting the tibial tray 102, the fastener 160, the connector 170, and the augment member 150 together.

It will be appreciated that the connector 170 may be attached to the head portion 162 of the fastener 160 such that at least a portion of the head portion 162 may be installed and inserted within the recess 112, to thereby fully permit the installation and insertion of the connector 170 within the recess 112. Additionally, the body member 168 of the fastener 160 may be installed within the recess 152 of the augment member 150. When the head portion 162 of the fastener 160 and the connector 170 are thus seated and installed within the recess 112, there may be a dimension within the recess 112, labeled as "A," that may be larger than a dimension labeled as "B" to ensure that there is enough clearance for the connector 170 to fully engage and contact the ledge 117, and possibly the wall 116, without bottoming out. Dimension "A" may be defined as a distance between a top surface 160a of the head portion 162 when installed within the recess 112, and the upper surface 112a of the recess 112. On the other hand, dimension "B" may be defined as a distance between the bottom surface 178 of the connector 170 and a top surface 164a of the retention lip 164 (illustrated best in FIG. 3B), as the bottom surface 178 of the connector 170 is in engagement with the ledge 117 (illustrated best in FIG. 3).

It will be appreciated that dimension "B" may also be driven, at least in part, by a height 171 of the connector 170. Accordingly, it will be appreciated that the connector 170 may be modified to include differing heights 171, but the height 171 of the connector 170 should not be modified such that dimension "B" may be larger than dimension "A."

Figure 5:
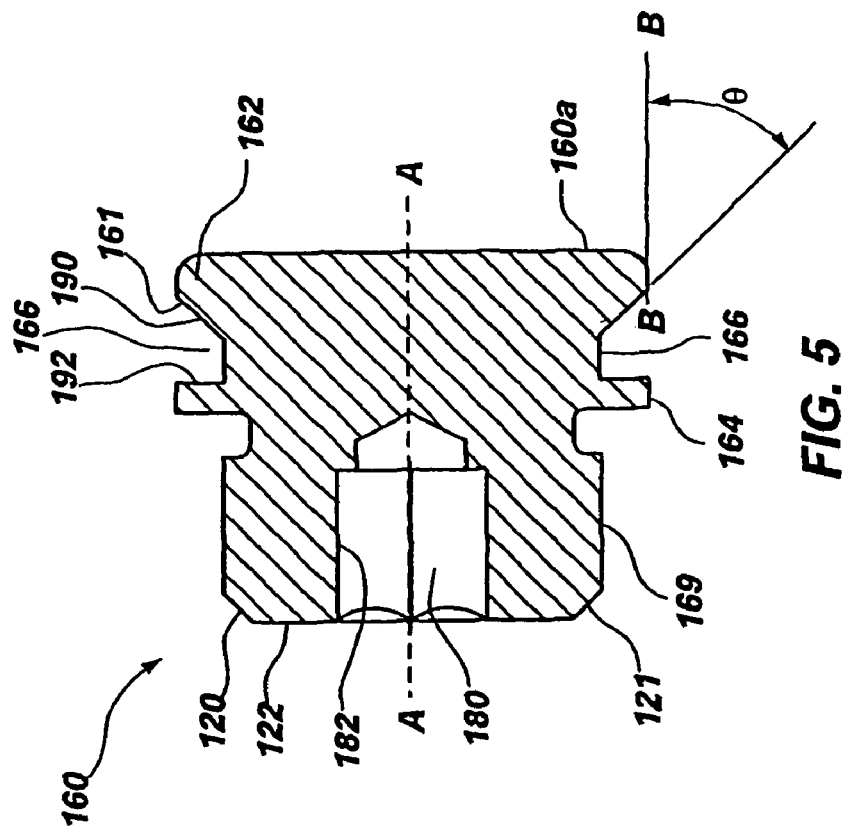
FIG. 5 is a side, cross-sectional view of the fastener of FIG. 4, taken along section A-A, made in accordance with the principles of the present disclosure.
Figure 4:
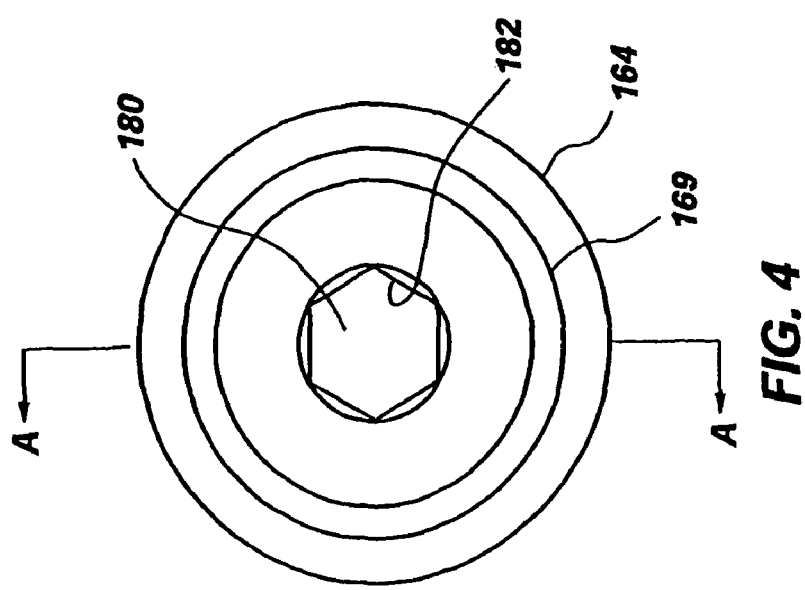
FIG. 4 is a bottom view of the fastener of FIG. 3, made in accordance with the principles of the present disclosure.

Referring simultaneously to FIGS. 3-5, the recess 112 of the tibial tray 102 may be configured and dimensioned to receive therein at least a portion of the fastener 160, which may be the head portion 162. The head portion 162 of the fastener 160 may comprise the frusto-conical surface 161 that may taper at an angle θ with respect to a line B-B that is parallel to a long axis A-A of the fastener 160, as illustrated in FIG. 5. It will be appreciated that the angle θ may be within a range from about fifteen degrees to about seventy-five degrees. For example, applicant has found that an angle θ within a range from about thirty degrees to about sixty degrees to be useful. More specifically, applicant has found that a range from about forty degrees to about fifty degrees, such as forty-five degrees, to be beneficial.

The frusto-conical surface 161 may lead into the multi-surface recess 166 from the top surface 160a of the head portion 162, and may further operate as an upper boundary 190 of the multi-surface recess 166. It will be appreciated that the frusto-conical surface 161 of the head portion 162 may also operate to permit the connector 170 to be compressed into the multi-surface recess 166 during insertion of the head portion 162 of the fastener 160 into the recess 112 of the tibial tray 102. It will be appreciated that a length of the frusto-conical surface 161 may be modified by one of skill in the art to include other lengths that may modify the size and shape of the multi-surface recess 166. As the length of the frusto-conical surface 161 is modified, other surfaces of components that may also form part of the multi-surface recess 166 may also be modified, such that the size and shape of the multi-surface recess 166 may change accordingly.

Referring now to FIG. 3b, the retention lip 164 of the fastener 160 may comprise the top surface 164a referred to above, a bottom surface 164b, and a side surface 164c connecting the top and bottom surfaces 164a and 164b, respectively. It will be appreciated that a length L1 of the top surface 164a of the retention lip 164 may be within a range from about sixty percent to about ninety percent of a length L2 of the frusto-conical surface 161. For example, the length L1 of the top surface 164a of the retention lip 164 may be within a range from about sixty-five percent to about eighty-five percent of the length L2 of the frusto-conical surface 161, and more specifically between a range from about seventy percent to about eighty percent of the length L2 of the frusto-conical surface 161. It will be appreciated that as the length L1 of the top surface of the retention lip 164 is modified, the length L2 of the frusto-conical surface 161 may also be modified accordingly to maintain the geometric relationship described above. It will be appreciated that the retention lip 164 may operate as a lower boundary 192 of the multi-surface recess 166.

As illustrated in FIGS. 3 and 3B, the retention lip 164 may be formed orthogonal to a wall 167 of the multi-surface recess 166. However, it will be appreciated that such a geometric configuration is not required, and the retention lip 164 may be formed at an angle with respect to the wall 167 that may be greater than or less than ninety-degrees. Accordingly, by modifying the orthogonal relationship of the retention lip 164 with the wall 167, the shape of the multi-surface recess 166 may also be modified. The retention lip 164 may function to retain the connector 170 within the multi-surface recess 166 during installation of the head portion 162 of the fastener 160 within the recess 112.

Those of skill in the art will recognize that a significant amount of the total force exerted on the fastener 160 may be distributed through the retention lip 164 to the augment member 150, when the augment member 150 is cinched up tightly against the bottom surface 110 of the component 100. Accordingly, it will be appreciated that a thickness 142 of the retention lip 164 may be modified to increase or decrease the strength of the retention lip 164. As the thickness 142 is increased, the retention lip 164 may be strengthened. Conversely, as the thickness 142 is decreased, the retention lip 164 may be weakened.

It will be appreciated that as the thickness 142 of the retention lip 164 increases or decreases, the corresponding dimension "B" may also be increased or decreased accordingly. It should be noted that the relationship stated above, where dimension "A" may be larger than dimension "B," may be maintained despite the modifications to the present disclosure in order for the fastener 160 to avoid bottoming out in the recess 112. For example, as the retention lip 164 decreases in thickness 142 and dimension "B" increases, dimension "A" may also need to be increased to maintain the relationship. It will be appreciated that there are a number of different engineering mechanisms by which dimension "A" may be increased, for example, by decreasing the head portion 162 of the fastener 160, and such modifications are intended to fall within the scope of the present disclosure.

As stated previously and illustrated most clearly in FIGS. 3A and 3B, the multi-surface recess 166 of the fastener 160 may be partially bound by the frusto-conical surface 161, which may operate as the upper boundary 190, and the top surface 164*a* of the retention lip 164, which may operate as the lower boundary 192. The multi-surface recess 166 may further be defined by the wall 167 referred to above, which may be formed between, and connect, the frusto-conical surface 161 of the head portion 162 and the top surface 164*a* of the retention lip 164.

The multi-surface recess 166 may operate to provide a location in which the connector 170 may be compressed, such that the connector 170 may have a compressed dimension that may be less than or substantially equal to the widest dimension D3 of the head portion 162 of the fastener 160. Accordingly, as the head portion 162 enters through the opening 114 of the recess 112, and the connector 170 is in an uncompressed state, the connector 170 may contact the tapered surface 115 of the ledge 117 compressing the connector 170 into the multi-surface recess 166, thus permitting the head portion 162 to be located and secured within the recess 112.

It will be appreciated that the shape of the multi-surface recess 166, as illustrated in FIGS. 3, 3A and 3B, may be such that as the body member 168 of the fastener 160 is tightened into the recess 152 of the augment member 150, and as the fastener 160 is tightened down into the augment member 150, the frusto-conical surface 161 of the head portion 162 may operate to exert a force on the connector 170. The force exerted by the frusto-conical surface 161 may be diagonal, such that the force is directed downwardly and outwardly and pushes the connector 170 down and out into the wall 116 of the recess 112 and against the ledge 117. Thus, the interference snap-fit between the connector 170, the ledge 117 and the wall 116 of the recess 112, and the frusto-conical surface 161 of the head portion 162 of the fastener 160 may be strengthened as the frusto-conical surface 161 engages the connector 170, and pushes the connector 170 downwardly and outwardly into contact with the wall 116 and the ledge 117.

It will be appreciated that the shape of the multi-surface recess 166 may be modified to be of any suitable shape, so long as the multi-surface recess 166 may provide a location in which the connector 170 may be compressed, such that the connector 170 may have a compressed dimension that may be less than or substantially equal to the widest dimension D3 of the head portion 162 of the fastener 160.

It will be appreciated that the body member 168 of the fastener 160 may comprise an outside surface 169, as illustrated in FIGS. 3 and 3A. The outside surface 169 of the body member 168 may comprise threads 169*a* thereon to provide the means for attaching the fastener 160 to the augment member 150. The body member 168 may further comprise a bottom surface 122 that may comprise a surface 120 forming a lead-in chamfer. The surface 120 forming the lead-in chamfer may be configured to permit the body member 168 to more easily enter into the recess 152 of the augment member 150 with minimal interference from portions of the augment member 150 surrounding the recess 152.

The body member 168 may also comprise a cavity 180 configured and dimensioned to receive the surgical instrument or tool 195 therein. It will be appreciated that the cavity 180 may be defined by an inner wall 182. The inner wall 182 of the cavity 180 may be star shaped, or shaped in a polygonal manner, for example square, pentagonal, hexagonal, octagonal or any other suitable polygonal shape, or otherwise, known in the art for engaging a corresponding instrument or tool. The surgical instrument 195 may comprise an outer surface 196 that may be configured and dimensioned to pass through the passage 184 of the augment member 150 and into the cavity 180 of the body member 168. Thus, the outer surface 196 may engage the inner wall 182 of the cavity 180 forming a friction fit, such that the surgical tool 195 may provide torque to the body member 168 of the fastener 160 driving the body member 168 into the recess 152 of the augment member 150. It will be appreciated that the surgical tool 195 may be shaped similarly to the cavity 180 such that the outer surface 196 may matingly engage the inner wall 182. For example, the tool 195 may be star shaped, or shaped in a polygonal manner, such as a square, pentagonal, hexagonal, octagonal or any other suitable polygonal shape, or otherwise shaped for engaging the inner wall 182.

The body member 168 of the fastener 160 may be configured and dimensioned to secure the augment member 150 to the tibial tray 102. Specifically, the threads 169*a* of the body member 168 may be configured for attaching the body member 168 to the recess 152 formed in the augment member 150. It will be appreciated that the threads 169*a* of the body member 168 may be arranged as reverse threads. As stated previously, the recess 152 of the augment member 150 may be defined by the sidewall 154, and the sidewall 154 may further comprise female threads 155 that may also be arranged as reverse threads, to matingly engage the threads 169*a* of the body member 168. The reverse nature of the threads 169*a* of the body member 168, and corresponding female threads 155 of the recess 152, permit the surgeon to turn the fastener 160, utilizing the surgical tool 195, from the bottom of the body member 168 in a standard, clockwise direction. As the threads 169*a* of the fastener 160 turn clockwise, the reverse nature of the threads 169*a*, and corresponding female threads 155, may permit the fastener 160 to tighten down into the recess 152 of the augment member 150 and also tighten down against the ledge 117, instead of the fastener 160 tightening up into the recess 112 of the tibial tray 102. Accordingly, the surgeon may be able to tighten the fastener 160 in a standard, intuitive manner into the recess 152 from the bottom of the body member 168, instead of from the top of the fastener 160, which would disadvantageously require the presence of a through hole in the tibial tray 102 in order to gain access to the top of the fastener 160 potentially creating a wear debris pathway.

The threads 169*a* of the body member 168 may matingly engage the threads 155 of the sidewall 154 of the recess 152, such that a secure fit between the body member 168 and the augment member 150 may be achieved. It will be appreciated that the connection between the body member 168 and the recess 152 is not required to be a threaded connection, but may be another connection known in the art to secure components to one another, such as a taper-fit, snap-fit, or press-fit. The augment member 150, after being connected and secured to the body member 168, may also be secured to the tibial tray 102, or other component, via the interference fit with the remainder of the fastener 160, i.e. the head portion 162.

Referring now to FIGS. 3, and 6-8, it will be appreciated that the head portion 162 of the fastener 160 may be secured within the recess 112 of the tibial tray 102 by the connector 170 via the interference fit. The connector 170, also referred to herein as a means for snap-fitting the head portion 162 to the recess 112 of the component 100 or 200, may comprise a first end 172, a second end 174, and may have a gap 176 formed between the first end 172 and the second end 174. It will be appreciated that the gap 176 may be large enough such that the connector 170 may be expanded to be inserted onto the head portion 162 of the fastener 160, without the connector 170 reaching its elastic limit and plastically deforming. It will also be appreciated that the gap 176 may be sized and dimensioned such that the connector 170 may be compressed without reaching its elastic limit. Therefore, it will be appreciated that the gap 176 may not be so small or so large such that plastic deformation occurs due to the connector 170 reaching its elastic limit as the connector 170 expands to be inserted onto the head portion 162 or contracts to be inserted into the multi-surface recess 166.

It will be appreciated that the gap 176 may have a linear distance between the first end 172 and the second end 174 that may be between a range from about forty-five percent to about ninety percent of a linear distance of an inner diameter of the connector 170. For example, a linear gap distance within a range from about fifty-five percent and about eighty percent of the linear distance of the inner diameter of the connector 170 has been found to be useful, and more specifically a range from about sixty percent to about seventy-five percent has been found to be useful. It will be appreciated that the gap 176 may be modified to include all distances that fall within the ranges stated above.

The connector 170 may be substantially circular in shape, similar to a ring with a slit, slot, or gap. However, it will be appreciated that the connector 170 may not be a completely enclosed ring, but may be interrupted by the gap 176, such that the connector 170 may be formed in an open ring configuration. It will further be appreciated that the connector 170 may be shaped in other configurations, besides a circular configuration, that are known, or that may become known in the future, in the art for providing an interference fit with other components, without departing from the scope of the present disclosure. For example, a square, pentagonal, hexagonal, octagonal, or any other polygonal shape may be utilized by the present disclosure for the shape of the connector 170. As used herein the term "connector" may be defined as any member of any shape that fits between the head portion 162 of the fastener 160 and the ledge 117 and wall 116 of the recess 112 to form an interference fit.

Figure 8:
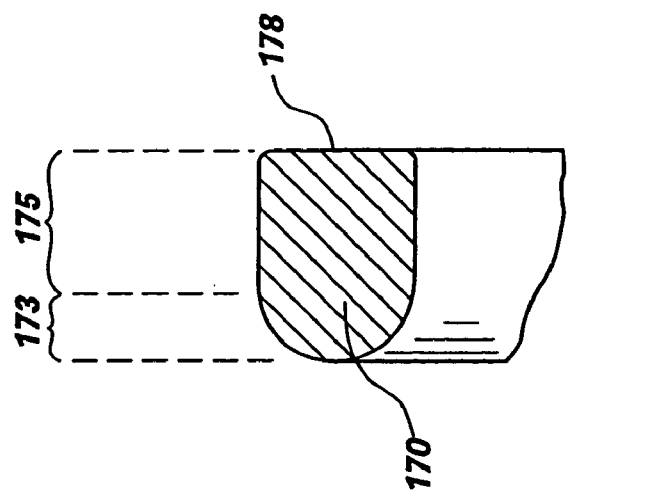
FIG. 8 is an enlarged, cross-sectional view of the connector of FIG. 7, taken from detail B.
Figure 7:
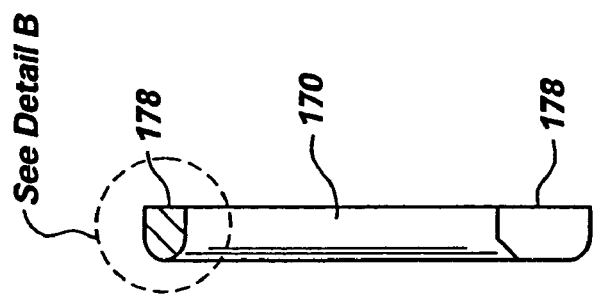
FIG. 7 is an end, partial cross-sectional view of the connector of FIG. 6, taken along section A-A.
Figure 6:
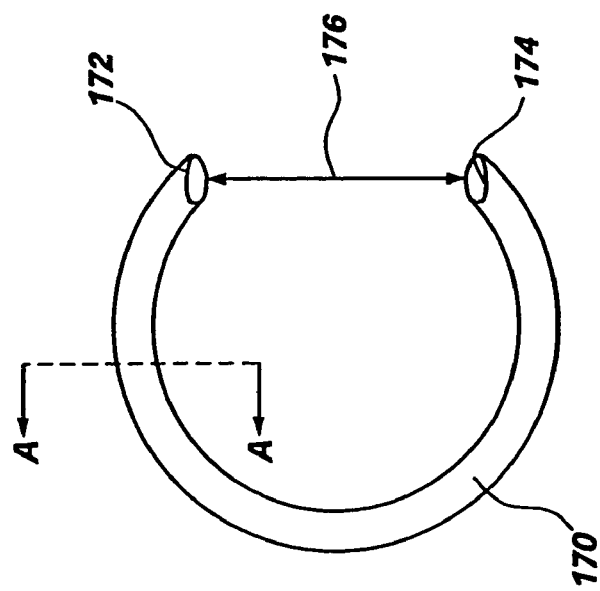
FIG. 6 is a top view of the connector of FIG. 3, made in accordance with the principles of the present disclosure.
Figure 9A:
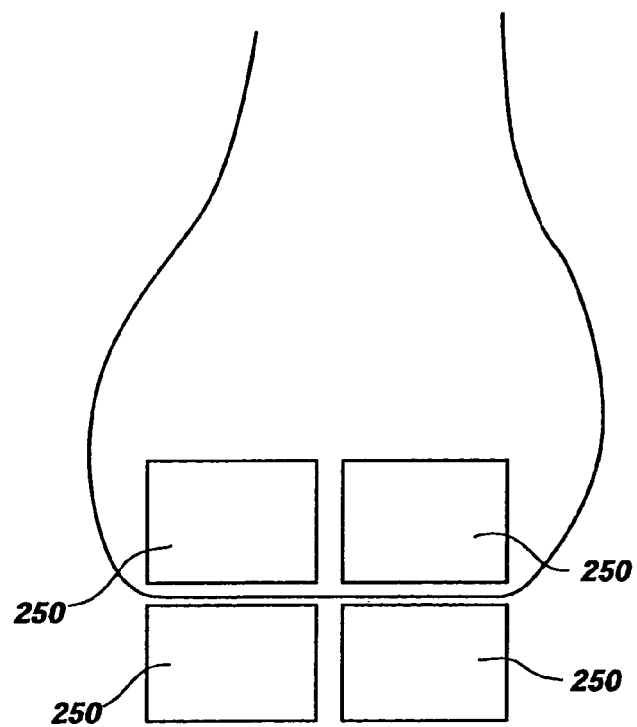
FIG. 9A depicts an example of an arrangement of four augment members.
Figure 9B:
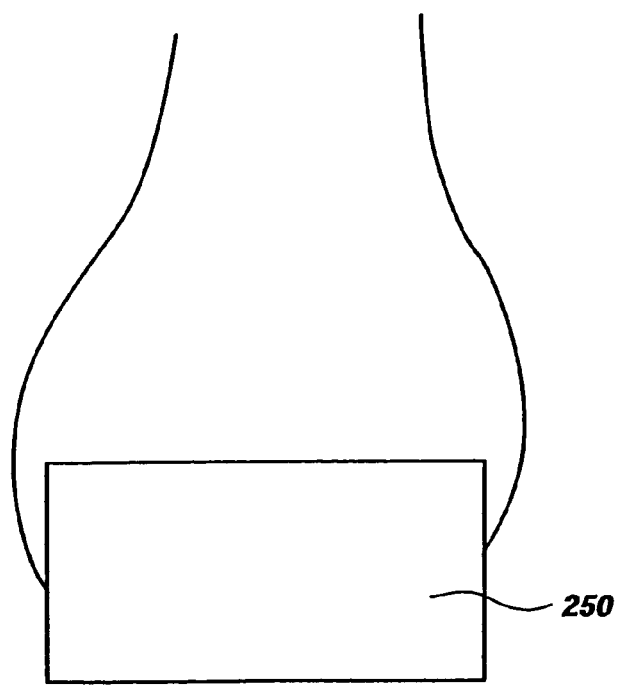
FIG. 9B depicts an example of an arrangement of a single augment member.

The connector 170 may comprise a cross-sectional shape that may be as illustrated in FIG. 8, wherein an upper portion 173 of the connector 170 may be substantially curvate, and a lower portion 175 may be substantially rectangular. However, it will be appreciated that other cross-sectional shapes may be utilized by the connector 170 without departing from the scope of the present disclosure. For example, the connector 170 may have a cross-sectional shape that is substantially circular, triangular, square, rectangular, or other suitable shapes known, or that may become known in the future, in the art for use as the connector 170.

The connector 170 may be manufactured from an elastic material, such that the connector 170 may expand and contract when a force is applied thereto. The connector 170 may also comprise an elastic memory, such that the connector 170 may be deformed and expanded to fit over or around the head portion 162 of the fastener 160. It will be appreciated that the connector 170 may be attached to the head portion 162 during the manufacturing process, before surgery, or even during surgery, and may fit into the multi-surface recess 166. It will be appreciated that due to its elastic memory, the connector 170 may substantially return to its original shape after being attached and inserted onto the head portion 162 of the fastener 160. Additionally, the elastic memory of the connector 170 may allow the connector 170 to be deformed and compressed to fit into an area, such as the multi-surface recess 166, without plastically deforming. It will be appreciated that the gap 176, in conjunction with the elasticity of the connector 170, may permit the connector 170 to be both expanded and compressed.

Figure 11:
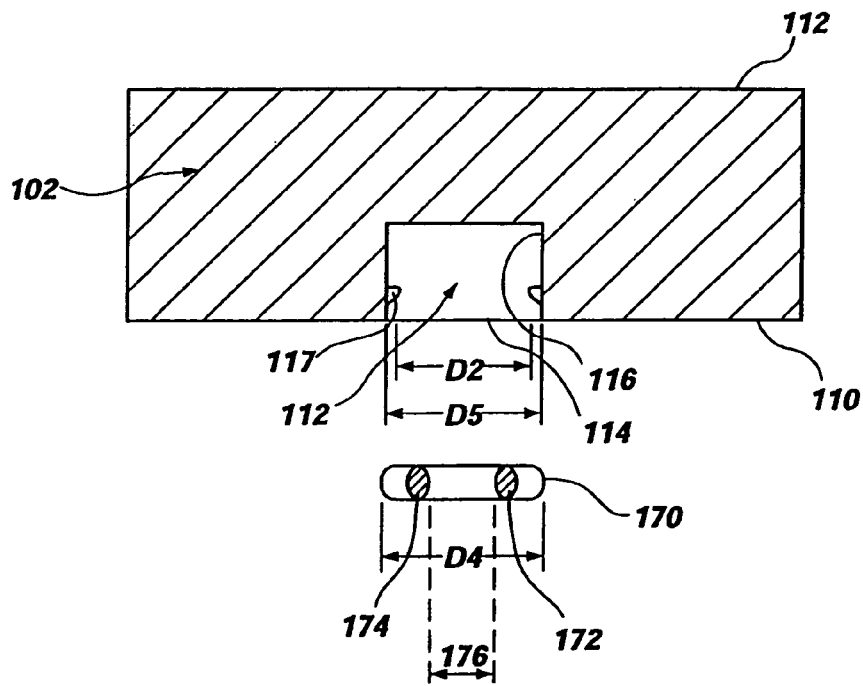
FIG. 11 is a side, cross-sectional view of the tibial tray, and a side view of the connector of the present disclosure.

As illustrated most clearly in FIG. 11, the connector 170 may be dimensioned such that it has a diameter "D4," in its original, undeformed state, that may be larger than a diameter of the recess 112 at its narrowest section, which may be represented by the dimension D2, in the tibial tray 102. It should be noted that the diameter D4 of the of the connector 170 may be smaller than, equal to, or larger than a diameter "D5" of the widest portion of the recess 112, which may be the distance between two points that are directly opposite each other on the wall 116 of the recess 112, and may be substantially similar to the width dimension W referred to above. It will be appreciated that as a compression force is applied to the connector 170, the first end 172 and the second end 174 may be brought close together, decreasing the size of the gap 176. Thus, the connector 170 may be compressed into the multi-surface recess 166 of the fastener 160 by a compression force that may be applied to the connector 170 by the surface 115 of the ledge 117, such that the diameter D4 of the connector 170 may become slightly smaller than the diameter D2 of the recess 112, as the head 162 of the fastener 160 enters through the opening 114 and into the recess 112.

Accordingly, as an upper most portion 162a of the head portion 162 of the fastener 160 passes through the opening 114 and into the recess 112, the connector 170 may contact the surface 115 of the ledge 117 of the recess 112, such that the connector 170 may be compressed into the multi-surface recess 166. As the head portion 162 continues to enter into the recess 112, the connector 170 may clear the ledge 117 permitting the connector 170, because of its elasticity, to substantially snap back to its original shape. As the connector 170 snaps substantially back to its original shape, the connector 170 may come into engagement with and contact the wall 116 of the recess 112. It will be appreciated that the connector 170 and wall 116 of the recess 112 may be dimensioned such that the connector 170 may return completely back to its original shape without engaging the wall 116 but may engage the top surface 117a of the ledge 117, or the connector 170 may return to its original shape engaging and contacting the wall 116, or the connector 170 may not fully return to its original shape, but may return substantially to its original shape being compressed slightly by the wall 116. In either case, there will be enough friction between the connector 170 and the top surface 117a of the ledge 117, or between the connector 170 and the wall 116 to form a secure connection. The engagement and contact of the connector 170 with the top surface 117a of the ledge 117, or the wall 116 of the recess 112 may form part of the interference snap-fit. Whereas, the complete interference snap-fit may occur between the frusto-conical surface 161 of the multi-surface recess 166, the connector 170, the top surface 117a of the ledge 117, and the wall 116 of the recess 112 of the tibial tray 102, thereby securing the fastener 160 to the tibial tray 102.

It will be appreciated that the connector 170 may be dimensioned such that as the body member 168 of the fastener 160 is tightened into the recess 152 of the augment member 150, a portion of the connector 170 may be forced by the frusto-conical surface 161 of the multi-surface recess 166 into the wall 116 of the recess 112, forming a more secure interference fit. As the connector 170 is forced further into engagement with the wall 116, the strength of the interference fit may be increased.

It should be noted that the material used to manufacture the connector 170 should possess characteristics of elastic memory, such that the connector 170 may elastically deform. The phrase "elastic memory" as used herein may be defined as the ability of a component to deform as a force is exerted thereon without plastically deforming, such that the component may substantially return to its original shape after the force is released. Therefore, the elastic memory of the material allows the connector 170 to substantially return to its original shape or position after deformation without plastically deforming. It should be noted that a slight amount of plastic deformation may occur in actuality, but will not be readily apparent to a human observer without the aid of instrumentation.

Therefore, the material should be capable of providing enough strength for the connector 170 to maintain its shape within the recess 112, thus securing the fastener 160 to the tibial tray 102 by way of the interference fit between the frusto-conical surface 161 of the multi-surface recess 166, the connector 170, the top surface 117a of the ledge 117, and the wall 116 of the recess 112 of the tibial tray 102. Further, the material of the connector 170 should be flexible enough to accommodate compression, such that the connector 170 may elastically deform, as the head portion 162 of the fastener 160 passes through the opening 114 of the recess 112, and the connector 170 contacts the surface 115 of the ledge 117 during initiation of said interference fit, as well as accommodate expansion during the installation of the connector 170 onto the head portion 162 of the fastener 160, without reaching its elastic limit.

In practice, the augment member 150 may be partially secured to the body member 168 of the fastener 160 prior to the attachment of the connector 170 and head portion 162 of the fastener 160 within the recess 112 of the tibial tray 102. After the head portion 162 has been inserted into the recess 112, and the interference snap-fit initiated, each of the augment members 150 may be secured and tightened to their respective body member 168, or body members 168 depending upon the number of connection sites per augment member 150, such that the augment member 150 may be cinched up tightly against the bottom surface 110 of the tibial tray 102. However, it should be noted that the above steps are not required to be performed in the exact order stated above. For example, the augment member 150 may not be partially or fully secured to the body member 168 until after the head portion 162 of the fastener 160, and the connector 170 may be secured within the recess 112 of the tibial tray 102.

It will be appreciated that each of the augment members 150 may be shaped to conform to the anatomical and surgical requirements of the patient. Accordingly, the augment members 150 may be provided in various shapes, sizes and dimensions, such that the augment members 150 may conform to a resected surface of the bone. As demonstrated by FIGS. 2 and 10A-10D, it will be appreciated that the geometric size and shape of the augment members 150 may be modified to include nearly any size and shape to conform to the specific needs of the patient. For example, the augment members may be shaped as a block (illustrated best in FIG. 2), or as a wedge (illustrated best in FIGS. 10A-10D), without departing from the scope of the present disclosure.

It will be appreciated that augment members 150 of different shapes, or of the same shape, may be used together. For example, a surgeon may use one wedge-shaped augment member 150 with one block-shaped augment member 150 to rebuild a portion of the tibia to form the desired joint line, or the surgeon may use two wedge-shaped augment members 150, or two block-shaped augment members 150. It will further be appreciated that a single wedge-shaped augment member 150 (illustrated best in FIG. 12) may be used, wherein the single augment member 150 may be configured and dimensioned to essentially cover the bottom surface 110 of the tibial tray 102.

Figure 12:
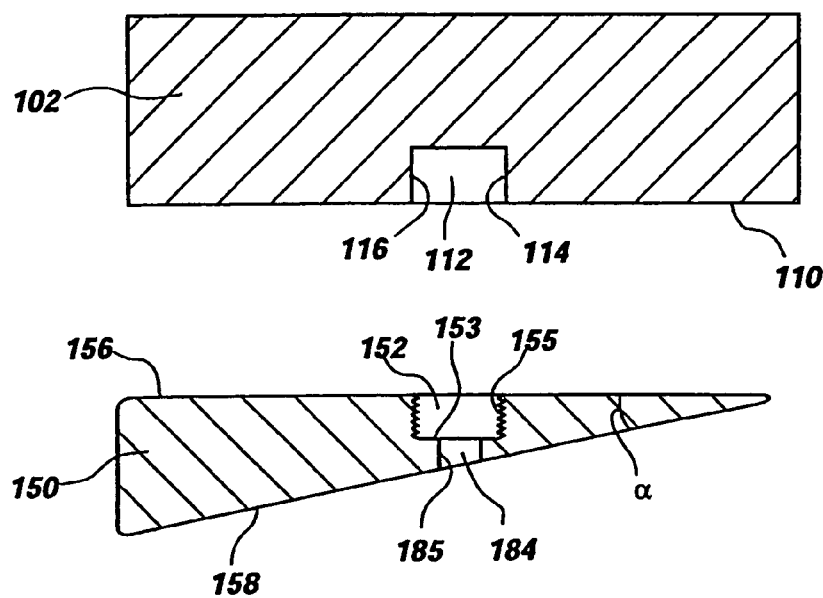
FIG. 12 is a side, cross-sectional view of the tibial tray and an alternative embodiment of the augment member of the present disclosure.

As illustrated most clearly in FIG. 12, the bottom surface 158 of the single wedge-shaped augment member 150 may taper at an angle α with respect to the top surface 156. Applicant has found that a bottom surface 158 that may taper at an angle α within a range from about ten degrees to about twenty degrees to be beneficial. For example, applicant has found that an angle α from about ten degrees, or about twelve degrees, or about fourteen degrees, or about sixteen degrees, or about eighteen degrees, or about twenty degrees to be beneficial.

It will be appreciated that each augment member 150 may be modified to include additional shapes and sizes. For example, one augment member 150 may be taller and/or wider than another augment member 150, or the augment members 150 may be essentially the same height and width, without departing from the scope of the present disclosure. The augment member 150 of FIG. 10A is illustrated as being both taller and wider than the augment member 150 of FIG. 10B. Additionally, the bottom surface of each of the augment members 150 illustrated in FIGS. 10A-10D, may taper at an angle β with respect to a line C-C that is parallel to the top surface 156. It will be appreciated that the angle β may be within a range from about ten degrees to about twenty degrees, similar to angle α referred to above. For example, applicant has found that an angle β from about ten degrees, or about twelve degrees, or about fourteen degrees, or about sixteen degrees, or about eighteen degrees, or about twenty degrees to be beneficial. It will be appreciated that the angle β may be various angles that correspond to the cuts made by the surgeon on the bone. It will further be appreciated that the bottom surface 158 of the block shaped augment members 150 may be substantially flat, as the surface contour of the bone may be substantially flat due to the surgeon's resection of the bone.

Referring now to FIGS. 3A, 10C-10D, and 12, wherein various augment members 150 are illustrated. It will be appreciated that the recess 152 may comprise a base 153 having the through passage 184 extending therefrom. The through passage 184 may be defined by sidewall 185, and may open on the bottom surface 158 of the augment member 150. The through passage 184 may be configured and dimensioned to permit the surgical tool 195 to pass through the passage 184 up through the recess 152, if necessary, and into the cavity 180 of the fastener 160. It will be appreciated that as the outer surface 196 of the surgical tool 195 is inserted into the cavity 180 of the body portion 168 and engages the inner wall 182, the surgeon may then begin to tighten the body member 168 of the fastener 160 into the recess 152 of the augment member 150. Accordingly, the through passage 184 may be dimensioned to permit the passage of the surgical tool 195 with minimal, or even without, interference from the sidewall 185.

It will be appreciated that the size and shape of the through passage 184 may be modified to be larger or smaller than illustrated. For example, the through passage 184 may be as wide as, or wider than, the recess 152 of the augment member 150, or the through passage 184 may be only as wide as the surgical tool 195, or the through passage 184 may be any width therebetween. Additionally, the shape of the through passage 184 may be modified to be circular, oval, square, star, pentagonal, hexagonal, octagonal, or any other suitable shape for permitting the passage of the surgical tool 195.

It will be appreciated that the snap-fit connection discussed above, may also be applied to other embodiments of the present disclosure. For example, a recess 212 may be formed in other components, which recess 212 may be similar to the recess 112 formed in the tibial component 100, such as a femoral component 200 (illustrated in FIG. 9), which femoral component 200 may be used as part of a prosthetic knee joint. It should be noted that the recess 212 may utilize the same structural features as the recess 112 discussed above in connection with the tibial component 100. Further, at least one augment member 250 may be attached to the femoral component 200 using the same structural features and in the same manner described above in connection with the tibial component 100. Therefore, the present disclosure may be modified and utilized on other components besides the tibial component 100, and such modifications are intended to fall within the scope of the present disclosure.

It will be appreciated that the number of augment members 250 used to support the femoral component 200 may be different than the number of augment members 150 used to support the tibial component 100. The at least one augment member 250 used on the femoral component 200 may comprise a plurality of augment members 250 that may be located on multiple sides of the femur. For example, the augment members 250 may be located on a posterior side, a medial side, and/or a lateral side of the femur by way of a distal connection between the component 200, the connector 170, the fastener 160, and the augment member 250. More specifically, the connection site of the augment members 250 may be on the distal portion of each of the condyles of the femur, and on the posterior portion of the femur above the condyles, such that there may be four augment members 250 connected to the distal femur. Namely, one augment member 250 per femoral condyle and located distally thereon, and one augment member 250 located posteriorly above each of the femoral condyles for a total of four augment members 250. It will be appreciated that there is potential for more or less than four augment members 250 to be attached to the femoral component 200.

It should be noted that the augment members 250 may be attached to the femoral component 200 by utilizing a distal connection site, and modifying the plurality of augment members 250 into a one-piece femoral augment 250. It will be appreciated that each of the augment members 150 and 250 of the present disclosure may be attached to their respective components 100 or 200 at a single connection site, or at multiple connection sites (illustrated best in FIG. 14), without departing from the scope of the present disclosure.

The design of the present disclosure may simplify the manufacturing of the components of the present disclosure by eliminating the use of threads in the recess 112 of the tibial or femoral component 100 or 200. Elimination of the threads in the recess 112 or 212, may eliminate a potentially difficult task of machining threads into a relatively shallow recess 112, as the recess 112 or 212 may not extend completely through the tibial or femoral component 100 or 200. It will be appreciated that the recess 112 or 212 formed in the tibial component 100 or femoral component 200 may be cast directly into the component 100 or 200 with minimal post-cast machining steps. Accordingly, the manufacture of the components or implants of the present disclosure may be advantageously simplified without adverse effects.

In accordance with the features and combinations described above, a useful method of connecting an augment member to an implant includes the steps of:

(a) providing an implant comprising a bottom surface with a recess defined by a wall formed therein, wherein the recess comprises a surface that protrudes slightly into the recess and tapers in a proximal-to-distal direction forming part of a ledge within the recess, wherein the implant further comprises an opening surrounding the recess;

(b) providing an elastic connector, a fastener, and at least one augment member, wherein the fastener comprises a head portion comprising a multi-surface recess formed therein, and a body portion, wherein the multi-surface recess is defined by an upper boundary, a lower boundary, and a connecting wall, wherein the at least one augment member comprises a recess configured and dimensioned to receive the body portion of the fastener therein;

(c) positioning the elastic connector around the head portion of the fastener, such that the elastic connector may be positioned at least partially within the multi-surface recess;

(d) compressing the elastic connector into the multi-surface recess as the head portion of the fastener is inserted through the opening and into the recess of the implant;

(e) forming an interference fit between the elastic connector, the ledge and wall of the recess, and the multi-surface recess of the fastener by permitting the elastic connector to decompress substantially back into its original shape, thereby contacting the wall of the recess; and (f) inserting the body portion of the fastener into the recess of the augment member to thereby bring the augment member into engagement with the bottom surface of the implant, such that the augment member is attached to said implant by said fastener.

In accordance with the features and combinations described above, another useful method of connecting an augment member to an implant includes the steps of:

(a) providing an implant comprising a bottom surface with a recess defined by a wall formed therein, wherein the recess comprises a surface that protrudes slightly into the recess and tapers in a proximal-to-distal direction forming part of a ledge within the recess, wherein the implant further comprises an opening surrounding the recess;

(b) providing an elastic connector, a fastener, and at least one augment member, wherein the fastener comprises a head portion comprising a multi-surface recess formed therein and a body portion, wherein the multi-surface recess is defined by an upper boundary, a lower boundary, and a connecting wall, wherein the at least one augment member comprises a recess configured and dimensioned to receive the body portion of the fastener therein;

(c) positioning the elastic connector around the head portion of the fastener, such that the elastic connector may be positioned at least partially within the multi-surface recess;

(d) inserting the body portion of the fastener into the recess of the augment member;

(e) compressing the elastic connector into the multi-surface recess as the head portion of the fastener is inserted through the opening and into the recess of the implant; and (f) forming an interference fit between the elastic connector, the ledge and wall of the recess, and the fastener by permitting the elastic connector to decompress substantially back into its original shape, to thereby bring the augment member into engagement with the bottom surface of the implant such that the augment member is attached to said implant by said fastener.

It will be appreciated that the structure and apparatus disclosed herein is merely one example of a means for attaching the fastener to the augment member, and it should be appreciated that any structure, apparatus or system for attaching the fastener to the augment member, which performs functions the same as, or equivalent to, those disclosed herein are intended to fall within the scope of a means for attaching the fastener to the augment member, including those structures, apparatus or systems for attaching which are presently known, or which may become available in the future. Anything which functions the same as, or equivalently to, a means for attaching the fastener to the augment member falls within the scope of this element.

It will be appreciated that the structure and apparatus disclosed herein is merely one example of a means for snap-fitting the head portion within the recess of the implant, and it should be appreciated that any structure, apparatus or system for snap-fitting the head portion to the recess, which performs functions the same as, or equivalent to, those disclosed herein are intended to fall within the scope of a means for snap-fitting the head portion within the recess of the implant, including those structures, apparatus or systems for snap-fitting the head portion to the recess which are presently known, or which may become available in the future. Anything which functions the same as, or equivalently to, a means for snap-fitting the head portion within the recess of the implant falls within the scope of this element.

It will be appreciated that the structure and apparatus disclosed herein is merely one example of a means for connecting the augment member to the implant, and it should be appreciated that any structure, apparatus or system for connecting the augment member to the implant, which performs functions the same as, or equivalent to, those disclosed herein are intended to fall within the scope of a means for connecting the augment member to the implant, including those structures, apparatus or systems for connecting the augment member to the implant which are presently known, or which may become available in the future. Anything which functions the same as, or equivalently to, a means for connecting the augment member to the implant falls within the scope of this element.

Those having ordinary skill in the relevant art will appreciate the advantages provided by the features of the present disclosure. For example, it is a potential feature of the present disclosure to provide an augment member and connector that may eliminate or reduce wear debris. A further potential feature of the present disclosure is to provide such an augment member and connector that may eliminate the use of threads, which may operate as stress risers, in a cavity or recess formed in an implant to receive the fastener and connector therein. It is yet a further potential feature of the present disclosure, in accordance with one aspect thereof, to provide a secure attachment between an implant, a fastener, and a connector, that may also reduce or eliminate wear debris. It is another potential feature of the present disclosure to provide a connection between the augment member, and the implant that is simple in design and manufacture. It is a potential feature of the present disclosure to provide a device that may allow a recess to be cast into an implant, for example a tibial or femoral implant, with limited post-cast machining steps.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An orthopedic system comprising:
   an implant member comprising a recess formed therein, wherein the recess is defined by a wall;
   a fastener comprising a head portion and a body member;
   an augment member configured to augment the implant member to rebuild a resected portion of bone on a patient, wherein the fastener connects the augment member to the implant member, wherein the body member comprises means for attaching the fastener to the augment member, and wherein the means for attaching the fastener to the augment member allows the augment member to be cinched up against the implant member; and
   means for snap-fitting the head portion of the fastener into the recess of the implant member, to thereby secure said fastener to said implant member, wherein the means for snap-fitting the head portion of the fastener into the recess of the implant member is not an integral part of the fastener, and wherein the system is configured such that, as the means for attaching the fastener to the augment member is used to cinch the augment member up against the implant member, the means for snap-fitting the head portion of the fastener into the recess of the implant member is forced into tighter engagement with a wall of the recess.

2. The system of claim 1, wherein the implant member comprises a top surface and a bottom surface, wherein the recess is formed within the bottom surface of the implant member, and wherein said recess extends partially between the top surface and the bottom surface of the implant member.

3. The system of claim 1, wherein the implant member is characterized by the absence of a through hole.

4. The system of claim 1, wherein the augment member comprises a top surface and a bottom surface, and at least one recess formed within the top surface, wherein the at least one recess is defined by a sidewall.

5. The system of claim 4, wherein the body member of the fastener is configured and dimensioned to be seated within the at least one recess of the augment member, to thereby secure the fastener to said augment member.

6. The system of claim 4, wherein the at least one recess of the augment member comprises a through passage.

7. The system of claim 6, wherein the at least one recess of the augment member comprises a base surface, wherein the through passage extends distally from the base surface through to the bottom surface of the augment member, such that the through hole is configured and dimensioned to permit a surgical instrument to pass therethrough.

8. The system of claim 4, wherein the sidewall of the at least one recess of the augment member comprises threads.

9. The system of claim 4, wherein the at least one recess of the augment member comprises a plurality of recesses, wherein each recess is defined by a sidewall.

10. The system of claim 4, wherein the bottom surface of the augment member slopes at an angle with respect to the top surface of the augment member, wherein the angle is within a range from about ten degrees to about twenty degrees.

11. The system of claim 10, wherein the angle is about ten degrees.

12. The system of claim 10, wherein the angle is about twelve degrees.

13. The system of claim 10, wherein the angle is about fourteen degrees.

14. The system of claim 10, wherein the angle is about sixteen degrees.

15. The system of claim 10, wherein the angle is about eighteen degrees.

16. The system of claim 10, wherein the angle is about twenty degrees.

17. The system of claim 1, wherein the augment member comprises a triangular cross-sectional shape, such that the augment member is substantially wedge-shaped.

18. The system of claim 1, wherein the augment member comprises a rectangular cross-sectional shape, such that the augment member is substantially block-shaped.

19. The system of claim 1, wherein the means for snap-fitting comprises a connector comprising a first end, and a second end with a gap formed between the first end and the second end.

20. The system of claim 19, wherein a linear distance between the first end and the second end of the gap is between a range from about forty-five percent to about ninety percent of a linear distance of an inner diameter of the connector.

21. The system of claim 20, wherein the linear distance of the gap is between a range from about fifty-five percent and about eighty percent of the linear distance of the inner diameter of the connector.

22. The system of claim 21, wherein the linear distance of the gap is between a range from about sixty percent to about seventy-five percent of the linear distance of the inner diameter of the connector.

23. The system of claim 1, wherein the means for snap-fitting is formed from an elastic material, such that the means for snap-fitting expands and contracts as a force is applied thereto.

24. The system of claim 1, wherein the means for snap-fitting is substantially circular in shape.

25. The system of claim 24, wherein the means for snap-fitting is interrupted by a gap, such that the means for snap-fitting is formed in an open ring configuration.

26. The system of claim 1, wherein the means for snap-fitting comprises an upper portion and a lower portion, wherein the upper portion comprises a cross-sectional shape that is substantially curvate, and wherein the lower portion comprises a cross-sectional shape that is substantially rectangular.

27. The system of claim 1, wherein the body member of the fastener comprises an outer surface containing threads thereon.

28. The system of claim 27, wherein the threads of the body member are configured and dimensioned as reverse threads.

29. The system of claim 28, wherein the augment member further comprises a sidewall defining a recess, wherein the sidewall comprises reverse threads for matingly engaging the reverse threads of the body member, such that the augment member is cinched up against a bottom surface of the implant member to thereby secure said augment member to said implant member.

30. The system of claim 1, wherein the body member further comprises a bottom surface, wherein the bottom surface of the body member comprises a cavity defined by a sidewall, wherein the cavity is configured and dimensioned to receive in engagement a surgical driving tool.

31. The system of claim 1, wherein the head portion of the fastener comprises a retention lip comprising a top surface, a bottom surface and a side surface.

32. The system of claim 31, wherein the head portion of the fastener further comprises a frusto-conical surface forming an upper boundary of a multi-surface recess.

33. The system of claim 32, wherein the top surface of the retention lip forms a lower boundary of the multi-surface recess, and wherein a wall connects the top surface of the retention lip with the frusto-conical surface forming a boundary of the multi-surface recess.

34. The system of claim 32, wherein the top surface of the retention lip has a length that is within a range from about sixty percent to about ninety percent of a length of the frusto-conical surface.

35. The system of claim 34, wherein the length of the top surface is about sixty-five percent to about eighty-five percent of the length of the frusto-conical surface.

36. The system of claim 35, wherein the length of the top surface is about seventy percent to about eighty percent of the length of the frusto-conical surface.

37. The system of claim 32, wherein the frusto-conical surface may taper at an angle with respect to the wall of the multi-surface recess, wherein the angle is within a range from about twenty degrees to about seventy-five degrees.

38. The system of claim 37, wherein the angle is within a range from about thirty degrees to about sixty degrees.

39. The system of claim 38, wherein the angle is within a range from about forty degrees to about fifty degrees.

40. The system of claim 39, wherein the angle is forty-five degrees.

41. The system of claim 1, wherein the head portion of the fastener comprises a multi-surface recess that is configured and arranged to receive the means for snap-fitting therein as a compression force is applied to the means for snap-fitting, wherein the head portion further comprises a retention lip that extends orthogonally with respect to a wall of the multi-surface recess.

42. The system of claim 1, wherein the recess of the implant member comprises a ledge that protrudes into the recess, the ledge comprising a top surface, a side surface, and a tapered surface, wherein the tapered surface tapers at an angle, with respect to the wall defining the recess, in a proximal-to-distal direction.

43. The system of claim 42, wherein the angle of the tapered surface is within a range from about thirty degrees to about sixty degrees.

44. The system of claim 43, wherein the angle of the tapered surface is within a range from about thirty-five degrees to about fifty-five degrees.

45. The system of claim 44, wherein the angle of the tapered surface is within a range from about forty degrees to about fifty degrees.

46. The system of claim 45, wherein the angle is about forty-five degrees.

47. The system of claim 42, wherein the ledge protrudes outwardly from the wall into the recess within a range from about one percent to about ten percent of a width of the recess of the implant member.

48. The system of claim 47, wherein the ledge protrudes outwardly within a range from about two percent to about eight percent of the width of the recess.

49. The system of claim 48, wherein the ledge protrudes outwardly within a range from about three percent to about five percent of the width of the recess.

50. The system of claim 42, wherein the ledge of the recess comprises a height dimension that is within a range from about five percent to about twenty percent of a height dimension of the recess of the implant member.

51. The system of claim 50, wherein the height dimension of the ledge is within a range from about ten percent to about fifteen percent of the height dimension of the recess.

52. The system of claim 51, wherein the height dimension of the ledge is within a range from about eleven percent to about thirteen percent of the height dimension of the recess.

53. The system of claim 1, wherein the implant member, the fastener, and the augment member are manufactured from a titanium alloy material.

54. The system of claim 1, wherein the wall of the recess of the implant member is characterized by an absence of threads.

55. The system of claim 1, wherein the means for snap-fitting comprises an outer dimension in an uncompressed state that is larger than a dimension between two points that are directly opposite one another on a side surface of a ledge of the recess of the implant member.

56. The system of claim 1, wherein the recess of the implant member comprises a ledge protruding outwardly from the wall of said recess, such that when the head portion of the fastener is fully installed within said recess, there is a distance within said recess between a top surface of the head portion, and an upper surface of the recess that is greater than a distance between a bottom surface of the means for snap-fitting, and a top surface of a retention lip of the fastener, as the bottom surface of the means for snap-fitting is in engagement with the ledge of said recess, and such that there is clearance for the means for snap-fitting to fully engage and contact the ledge without bottoming out.

57. The system of claim 1, wherein the means for snap-fitting is manufactured from an elastic material and comprises a diameter, and the head portion of the fastener comprises a diameter, wherein the diameter of the means for snap-fitting and the diameter of the head portion in combination are configured and arranged to enable the means for snap-fitting to be expandably placed on the fastener without expanding the means for snap-fitting beyond its elastic limit, and without compressing the means for snap-fitting beyond its elastic limit as the means for snap-fitting is located within a multi-surface recess of the fastener.

58. The system of claim 1, wherein the recess of the implant member is dimensioned such that a height dimension of the recess is within a range from about fifteen percent to about one-hundred percent of a width dimension of said recess.

59. The system of claim 58, wherein the height dimension of the recess of the implant member is within a range from about twenty percent to about eighty percent of the width dimension.

60. The system of claim 59, wherein the height dimension of the recess of the implant member is within a range from about twenty-five percent to about seventy-five percent of the width dimension.

61. The system of claim 60, wherein the height dimension of the recess of the implant member is within a range from about thirty-three percent to about sixty-seven percent of the width dimension.

62. The system of claim 61, wherein the height dimension of the recess of the implant member is within a range from about forty percent to about sixty percent of the width dimension.

63. The orthopedic system of claim 1, further comprising a second augment member, wherein the second augment member has at least one of a different shape and a different size than the augment member, and wherein the second augment member is configured to be connected to the implant member with the fastener.

64. The orthopedic system of claim 1, wherein the augment member is configured to be connected to the implant member along only a portion of a bottom surface of the implant member.

65. An orthopedic system comprising:
an augment member;
a connector;
an implant member comprising a top and bottom surface, the implant member further comprising a recess formed therein, wherein the recess is defined by a wall, wherein the recess comprises a protrusion extending outwardly from the wall;
a means for connecting the augment member to the implant member, wherein the means for connecting comprises a head portion;
wherein the connector and the head portion of the means for connecting are configured and arranged to be inserted into the recess, such that said connector and a part of the head portion of the means for connecting passes by the protrusion, permitting the connector to form an interference fit with said protrusion and said head portion, thereby securing the means for connecting to the implant member wherein the interference fit increases as the fastener is engaged with the augment member.

66. The system of claim 65, wherein the connector is formed from an elastic material, such that the connector expands and contracts as a force is applied thereto.

67. An orthopedic system comprising:
an elastic connector;
an implant member configured and dimensioned as part of a prosthetic joint, wherein the implant member comprises a sidewall defining a recess;
a fastener configured and dimensioned to attach the implant member to an augment member, wherein the fastener is a separate component from the elastic connector, wherein the fastener comprises a head portion comprising a retention lip and a multi-surface recess, wherein the multi-surface recess is defined by a frusto-conical surface, a wall, and a top surface of the retention lip;
wherein the elastic connector is dimensioned to be compressed into the multi-surface recess as an external force is applied to the elastic connector as the head portion of the fastener is inserted into the recess of the implant member, wherein the system is configured such that the elastic connector forms an interference fit with the multi-surface recess, and wherein the interference fit increases as the fastener is engaged with an augment member.

68. A method of connecting an augment member to an implant member, the method including the steps of:
(a) providing a fastener, connector, augment member, and implant member, wherein the augment member is configured to augment the implant member to rebuild a resected portion of bone on a patient, wherein the implant member comprises a recess defined by a wall, wherein the fastener comprises a head portion, and wherein at least a portion of the connector is attached to the head portion of the fastener;
(b) attaching the fastener to the augment member;

(c) inserting the head portion of the fastener into the recess of the implant member, such that the connector snap-fits into and forms an interference fit within said recess, thereby connecting said fastener to said implant member and connecting the implant member to the augment member; and (d) cinching the augment member against the implant member by tightening the fastener within the augment member, wherein the step of cinching the augment member causes the strength of the interference fit to be increased.

69. A method of connecting an augment member to an implant member, the method including the steps of:

(a) providing a fastener, elastic connector, implant member, and augment member, wherein the implant member comprises a surface with a first recess formed therein and the first recess is defined by a wall, wherein the fastener comprises a head portion and a body portion, wherein at least a portion of the elastic connector is attached to the head portion of the fastener, wherein the augment member comprises a second recess configured and dimensioned to receive the body portion of the fastener therein;

(b) inserting the head portion of the fastener into the first recess of the implant member, such that the elastic connector snap-fits into and forms an interference fit within said first recess, thereby connecting said fastener to said implant member;

(c) threadably attaching the body portion of the fastener to the second recess of the augment member, such that the augment member is cinched against and brought into engagement with the implant member, thereby connecting said augment member to said implant member; wherein the step of threadably attaching the body portion of the fastener to the second recess of the augment member causes the strength of the interference fit to be increased.

70. The method of claim 69, wherein the first recess of the implant member is located in a bottom surface of the implant member.

71. The method of claim 69, wherein the first recess comprises a surface that protrudes into the first recess, and tapers in a proximal-to-distal direction forming part of a ledge within said first recess, and wherein the implant member further comprises an opening surrounding said first recess.

72. The method of claim 71, wherein the head portion of the fastener comprises a multi-surface recess defined by a frusto-conical upper boundary, a lower boundary, and a wall connecting the upper boundary and the lower boundary.

73. The method of claim 72, wherein the elastic connector is compressed into the multi-surface recess as the head portion of the fastener is inserted through the opening and into said first recess of the implant member.

74. The method of claim 73, wherein an interference fit between the elastic connector, the ledge, the wall of the first recess, and at least a portion of the multi-surface recess of the fastener is formed when the elastic connector decompresses substantially back into its original shape, thereby contacting said wall of said first recess.

75. The method of claim 74, wherein the body portion of the fastener is inserted into the second recess of the augment member to thereby bring the augment member into engagement with a bottom surface of the implant member, such that the augment member is attached to said implant member by said fastener.

76. The method of claim 69, wherein the head portion of the fastener comprises a multi-surface recess defined by an upper boundary, a lower boundary, and a connecting wall.

77. The method of claim 68, further comprising:
providing a second augment member having at least one of a different shape and a different size than the augment member;
attaching a second fastener to the second augment member;
inserting the head portion of the second fastener into the recess of the implant member, such that the connector snap-fits into said recess, thereby connecting said second fastener to said implant member and connecting the implant member to the second augment member.

78. An orthopedic system comprising:
an implant member comprising a top surface, a bottom surface, and a recess formed in the bottom surface;
wherein the recess is defined by a wall;
wherein said recess extends partially between the top surface and the bottom surface of the implant member;
wherein the implant member is characterized by the absence of a through hole;
wherein the recess comprises a ledge comprising a top surface, a side surface, and a tapered surface that protrudes into the recess, wherein the tapered surface tapers at an angle, with respect to the wall defining the recess, in a proximal-to-distal direction;
wherein the angle of the tapered surface is within a range from about thirty degrees to about sixty degrees;
wherein the wall of the recess is characterized by an absence of threads;
an augment member;
a fastener comprising a head portion and a body member, wherein the fastener is configured and dimensioned to connect the augment member to the implant member; and
wherein the body member comprises an outer surface containing threads thereon, wherein the threads of the body member are arranged as reverse threads;
wherein the body member further comprises a bottom surface, wherein the bottom surface of the body member comprises a cavity defined by a sidewall, wherein the cavity is configured and dimensioned to receive in engagement a surgical driving tool;
wherein the head portion of the fastener comprises a retention lip comprising a top surface, a bottom surface and a side surface, and wherein the head portion further comprises a multi-surface recess;
wherein the head portion of the fastener further comprises a frusto-conical surface;
wherein a wall connects the top surface of the retention lip with the frusto-conical surface forming a boundary of the multi-surface recess, wherein the frusto-conical surface forms an upper boundary of the multi-surface recess, and the top surface of the retention lip forms a lower boundary of the multi-surface recess;
wherein the top surface of the retention lip has a length that is within a range from about sixty percent to about ninety percent of a length of the frusto-conical surface;
wherein the frusto-conical surface may taper at an angle with respect to the wall of the multi-surface recess, the angle being within a range from about twenty degrees to about seventy-five degrees;
wherein the augment member comprises a top surface and a bottom surface, and at least one recess formed within the top surface of the augment member, wherein the at least one recess is defined by a sidewall, and wherein the at least one recess of the augment member comprises a base surface;

wherein the at least one recess of the augment member comprises a through passage;

wherein the through passage extends distally from the base surface through to the bottom surface of the augment member, such that the through hole is configured and dimensioned to permit the surgical driving tool to pass therethrough and into the cavity of the fastener;

wherein the sidewall of the at least one recess of the augment member comprises threads, wherein the threads are arranged as reverse threads for matingly engaging the reverse threads of the body member of the fastener, such that the augment member cinches up against the bottom surface of the implant member to thereby secure said augment member to said implant member;

wherein the bottom surface of the augment member slopes at an angle with respect to the top surface of the augment member, wherein the angle is within a range from about ten degrees to about twenty degrees; and a means for snap-fitting the head portion of the fastener into the recess of the implant member, to thereby secure said fastener to said implant member;

wherein the means for snap-fitting comprises a connector comprising a first end, and a second end with a gap formed between the first end and the second end;

wherein a distance between the first end and the second end of the gap is between a range from about fifteen percent to about fifty percent of a diameter of the connector;

wherein the means for snap-fitting is formed from an elastic material, such that the means for snap-fitting expands and contracts as a force is applied thereto;

wherein the means for snap-fitting is substantially circular in shape, and formed in an open ring configuration;

wherein the means for snap-fitting comprises an upper portion and a lower portion, wherein the upper portion comprises a cross-sectional shape that is substantially curvate, and wherein the lower portion comprises a cross-sectional shape that is substantially rectangular;

wherein the means for snap-fitting comprises an outer dimension in an uncompressed state that is larger than a dimension between two points that are directly opposite one another on the side surface of the ledge of the recess of the implant member;

wherein the means for snap-fitting comprises a diameter, and the head portion of the fastener comprises a diameter, wherein the diameter of the means for snap-fitting and the diameter of the head portion in combination are configured and arranged to enable the means for snap-fitting to be expandably placed on the fastener without expanding the means for snap-fitting beyond its elastic limit, and without compressing the means for snap-fitting beyond its elastic limit as the means for snap-fitting is located within the multi-surface recess of the fastener;

wherein the ledge protrudes outwardly from the wall of the recess of the implant member, such that when the head portion of the fastener is fully installed within said recess of said implant member, there is a distance within said recess between a top surface of the head portion, and an upper surface of the recess of the implant member that is greater than a distance between a bottom surface of the means for snap-fitting, and the top surface of the retention lip of the fastener, as the bottom surface of the means for snap-fitting is engaged with the ledge of said recess of said implant member, such that there is clearance for the means for snap-fitting to fully engage and contact said ledge without bottoming out.

79. An orthopedic system comprising:

an implant member comprising a recess formed therein, said recess being defined by at least one wall;

a fastener comprising a head portion and a body member, wherein the fastener connects an augment member to the implant member; and an elastic connector configured and dimensioned to retain the head portion of the fastener within the recess of the implant member, to thereby secure said fastener to said implant member, wherein the system is configured such that the elastic connector forms an interference fit with the recess, and wherein the interference fit increases as the fastener is engaged with an augment member.

\* \* \* \* \*